US007491506B2

(12) United States Patent
Karin et al.

(10) Patent No.: US 7,491,506 B2
(45) Date of Patent: Feb. 17, 2009

(54) INHIBITION OF B-CELL MATURATION AND ANTIBODY PRODUCTION

(75) Inventors: Michael Karin, La Jolla, CA (US); Uwe Senftleben, Obereldingen (DE); Yixue Cao, San Diego, CA (US)

(73) Assignee: The Regents Of The University Of California, Oakland, CA (US)

( * ) Notice: Subject to any disclaimer, the term of this patent is extended or adjusted under 35 U.S.C. 154(b) by 306 days.

(21) Appl. No.: 11/330,582

(22) Filed: Jan. 11, 2006

(65) Prior Publication Data
US 2006/0105414 A1 May 18, 2006

Related U.S. Application Data

(63) Continuation of application No. 10/176,789, filed on Jun. 21, 2002, now abandoned.

(60) Provisional application No. 60/300,109, filed on Jun. 21, 2001.

(51) Int. Cl.
*C12Q 1/48* (2006.01)
(52) U.S. Cl. .................................................. 435/15
(58) Field of Classification Search .................. 435/15
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,965,188 A | 10/1990 | Mullis et al. |
| 5,225,347 A | 7/1993 | Goldberg |
| 5,246,921 A | 9/1993 | Reddy et al. |
| 5,500,357 A | 3/1996 | Taira et al. |
| 5,527,895 A | 6/1996 | Hampel et al. |
| 5,545,806 A | 8/1996 | Lonberg et al. |
| 5,569,825 A | 10/1996 | Lonberg et al. |
| 5,625,126 A | 4/1997 | Lonberg et al. |
| 6,252,043 B1 | 6/2001 | Hession et al. |

FOREIGN PATENT DOCUMENTS

EP     140 308     5/1985

OTHER PUBLICATIONS

Gibson et al., "A Novel Method for Real Time Quantitative RT-PCR," Genome Res. 6:995 (1996).
Maniatis et al. "Regulation of Inducible and Tissue-Specific Gene Expression," Science 236:1237 (1987).
Sambrook et al., *Molecular Cloning: A Laboratory Manual*, 2nd ed., Cold Spring Harbor Laboratory Press, New York, pp. 16.7-16.8 (1989).
Anderson and Young, Quantitative Filter Hybridization, in *Nucleic Acid Hybridization* (1985).
Sambrook et al., *Molecular Cloning: A Laboratory Manual*, Cold Spring Harbor Press, NY, pp. 9.31-9.58 (1989).
Sambrook et al., *Molecular Cloning: A Laboratory Manual*, Cold Spring Harbor Press, NY, pp. 7.39-7.52 (1989).
Crowther, "Enzyme-Linked Immunosorbent Assay (ELISA)," in *Molecular Biomethods Handbook*, Rapley et al. [eds.], pp. 595-617, Humana Press, Inc., Totowa, NJ (1998).
Harlow and Lane (eds.), *Antibodies: A Laboratory Manual*, Cold Spring Harbor Laboratory Press (1988).
Ausubel et al. (eds.), *Current Protocols in Molecular Biology*, Ch. 11, John Wiley & Sons, Inc., New York (1994).
Ghosh et al., "NF-κB and Rel Proteins: Evolunionarily Conserved Mediators of Immune Responses," Ann. Rev. Immunol. 16:255-260 (1998).
Rothwarf and Karin, "The NF-κB Activation Pathway: A Paradigm in Information Transfer from Membrane to Nucleus," Science Signal Transduction Knowledge Environment (STKE) (1999).
Karin et al., "Phosphorylation Meets Ubiquitination: The Control of NF-κB Activity," Ann. Rev. Immunol. 18:621 (2000).
Palombella et al., "The Ubiquitin-Proteasome Pathway is Required for Processing the NF-κB1 Precursur Protein and the Activation of NF-κB," Cell 78:773, 1994.
Mercurio et al., "p105 and p98 precursor proteins play an active role in NF-κB-mediated signal transduction," Genes Develop. 7:705 (1993).
Lin et al., "Cotranslational Biogenesis of NF-κB p50 by the 26S Proteasome," Cell 92:819 (1998).
Dumitru et al., "TNF-α Induction by LPS Is Regulated Post-transcriptionally via a TP12/ERKDependent Pathway," Cell 103:1071 (2000).
Liou et al., "Sequential Induction of NF-κB/Rel Family Proteins during B-Cell Terminal Differentiation," Mol. Cell. Biol. 14:5349 (1994).
Yamada et al., "Abnormal Immune Function of Hemopoietic Cells from Alymphoplasia (*aly*) Mice, a Natural Strain with Mutant NF-κB-Inducing Kinase," J. Immunol. 165:804 (2000).
Shinkura et al., "Alymphoplasia is caused by a point mutation in the mouse gene encoding Nf-κb-inducing kinase,"Nat. Genet. 22:74 (1999).
Yin et al., "Defective Lymphotoxin-β Receptor-Induced NF-κB Transcriptional Activity in NIK-Deficient Mice," Science 291:2162 (2001).
Xiao et al., "NF-κB-Inducing Kinase Regulates the Processing of NF-κB2 p100," Mol. Cell. 7:401 (2001).
Malinin et al., "MAP3K-related kinase involved in NF-κB induction by TNF, CD95 and IL-1," Nature 385:540-4 (1997).
Zandi et al.,"The IκB kinase complex (IKK) contains two kinase subunits, IKKα, and IKKβ, necessary for IκB phosphorylation and NF-κB activation," *Cell* 91:243-252 (1997).
Zandi et al., "Direct Phosphorylation of IκB by IKKα and IKKβ: Discrimination Between Free and NF-κB-Bound Substrate," 281:1360 (1998).
Mercurio et al., "IKK-1 and IKK-2: Cytokine-Activated IκB Kinases Essential for NK-κB Activation," Science 278:860 (1997).

(Continued)

*Primary Examiner*—Maryam Monshipouri
(74) *Attorney, Agent, or Firm*—Medlen & Carroll, LLP

(57) ABSTRACT

The present invention provides methods and compositions for the inhibition of B-cell maturation and antibody production without interfering with innate or T-cell mediated immunity.

12 Claims, 11 Drawing Sheets

OTHER PUBLICATIONS

Woronicz et al., "IκB Kinase-β: NF-κB Activation and Complex Formation with IκB Kinase-α and NIK," Science 278:866 (1997).

Li et al., "Severe Liver Degeneration in Mice Lacking the IκB Kinase 2 Gene," Science 284:321 (1999).

Li et al., "The IKKβ Subunit of IκB Kinase (IKK) is Essential for Nuclear Factor κB Activation and Prevention of Apoptosis," J. Exp. Med. 189:1839 (1999).

Tanaka et al., "Embryonic Lethality, Liver Degeneration, and Impaired NF-κB Activation in IKK-β-Deficient Mice," Immunity 10:421-429 (1999).

Chu et al., "JNK2 and IKKβ Are Required for Activating the Innate Response to Viral Infection," Immunity 11:721 (1999).

Senftleben et al., "IKKβ Is Essential for Protecting T Cells from TNFα-Induced Apoptosis," Immunity 14:217 (2001).

Hu et al., "Abnormal morphogenesis but intact IKK activation in mice lacking the IKKα subunit of IκB kinase," Science 284:316-320 (1999).

Takeda et al., "Limb and skin abnormalities in mice lacking IKKα," Science 284:313-316 (1999).

Hu et al., "IKKα controls formation of the epidermis independently of NF-κB," Nature 410:710 (2001).

Lu et al., "The antibacterial arm of the *Drosophila* innate immune response requires an IκB kinase," Genes Develop. 15:104 (2001).

Kaisho et al., "IκB Kinase α Is Essential for Mature B Cell Development and Function," J. Exp. Med. 193:417 (2001).

Caamano et al., "Nuclear Factor (NF)-κB2 (p100/p52) Is Required for Normal Splenic Microarchitecture and B Cell-mediated Immune Responses," J. Exp. Med. 187:185 (1998).

Franzoso et al., Mice Deficient in Nuclear Factor (NF)-κB/p52 Present with Defects in Humoral Responses, Germinal Center Reactions, and Splenic Microarchitecture, J. Exp. Med. 187:147 (1998).

Fütterer et al., "The Lymphotoxin β Receptor Controls Organogenesis and Affinity Maturation in Peripheral Lymphoid Tissues," Immun. 9:59 (1998).

Yan et al., "Identification of a receptor for BLyS demonstrates a crucial role in humoral immunity," Nat. Immun. 1:37 (2000).

Ling et al., "NF-B-inducing kinase activates IKK- by phosphorylation of Ser-176," Proc Natl Acad Sci USA 95: 3792-3797 (1998).

Huse et al., "Generation of a Large Combinatorial Library of the Immunoglobulin Repertoire in Phage Lambda," Science 246:1275-1281 (1989).

Winter and Harris, "Humanized antibodies," Immunol. Today 14:243-246 (1993).

Ward et al., "Binding activities of a repertoire of single immunoglobulin variable domains secreted from *Escherichia coli*," Nature 341:544-546 (1989).

Markus-Sekura, "Techniques for Using Anitsense Oligodeoxyribonucleotides to Study Gene Expression," Anal. Biochem. 172:289-295 (1988).

Hambor et al., "Functional Consequences of Anti-Sense RNA-Mediated Inhibition of CD8 Surface Expression in a Human T Cell Clone," J. Exp. Med. 168:1237-1245 (1988).

Genbank Sequence Accession No. AF080157 (1999).

Kruger et al., "Self-Splicing RNA: Autoexcision and Autocyclization of the Ribosomal RNA Intervening Sequence of Tetrahymena," Cell 31: 147-157 (1982).

Guerrier-Takada et al., "The RNA Moiety of Ribonuclease P is the Catalytic Subunit of the Enzyme," Cell 35: 849-857 (1983).

Wu et al., "Reversible Cleavage and Ligation of Hepatitis Delta Virus RNA," Science 243:652-655 (1989).

Hofacker et al., "Fast Folding and Comparison of RNA Secondary Structures," Monatshefte F. Chemie 125:167-188 (1994).

McCaskill, "The Equilibrium Partition Function and Base Pair Binding Probabilities for RNA Secondary Structure," Biopolymers 29:1105-1119 (1990).

Sioud and Drlica, "Prevention of human immunodeficiency virus type 1 integrase expression in *Escherichia coli* by a ribozyme," Proc. Natl. Acad. Sci. USA 88:7303-7307 (1991).

Molecular and Cellular Biology, Stephen L. Wolfe (Ed.), Wadsworth Publishing Company, p. 575 (1993).

Puttaraju et al., "A circular trans-acting hepatitis delta virus ribozyme," Nucl. Acids Res. 21:4253-4258 (1993).

Pitot, in "Fundamentals of Oncology," Marcel Dekker (Ed.), New York pp. 15-28 (1978).

Silverman et al., "A *Drosophila* IκB kinase complex required for Relish cleavage and antibacterial immunity," Genes Develop. 14:2461 (2000).

FIGURE 7

Analysis of NF-κB Target Gene Expression in Wild-Type and *Ikkα^AA^* B Cells

| Cells | Time | IκBα | TNFα | NFκB2 | Cyclin D2 | bcl-2 | MIP-1α | iNOS | RANK-L |
|---|---|---|---|---|---|---|---|---|---|
| WT | 1 hour | 2.05 | 4.97 | 0.51 | 1.14 | 1.77 | 3.35 | 4.38 | 8.87 |
| | 4 hours | 1.87 | 2.78 | 1.07 | 5.45 | 1.14 | 2.01 | 2.20 | 3.26 |
| IKKα^AA^ | 1 hour | 0.80 | 3.37 | 1.18 | 1.58 | 0.76 | 0.73 | 0.44 | 0.28 |
| | 4 hours | 0.85 | 2.06 | 1.31 | 5.77 | 0.83 | 0.80 | 0.44 | 0.11 |

FIG. 9

A. IKKα amino acid sequence (GENBANK NO. AF080157)

MERPPGLRPGAGGPWEMRERLGTGGFGNVCLYQHRELDLKIAIK

SCRLELSTKNRERWCHEIQIMKKLNHANVVKACDVPEELNILIHDVPLLAMEYCSGGD

LRKLLNKPENCCGLKESQILSLLSDIGSGIRYLHENKIIHRDLKPENIVLQDVGGKII

HKIIDLGYAKDVDQGSLCTSFVGTLQYLAPELFENKPYTATVDYWSFGTMVFECIAGY

RPFLHHLQPFTWHEKIKKKDPKCIFACEEMSGEVRFSSHLPQPNSLCSLIVEPMENWL

QLMLNWDPQQRGGPVDLTLKQPRCFVLMDHILNLKIVHILNMTSAKIISFLLPPDESL

HSLQSRIERETGINTGSQELLSETGISLDPRKPASQCVLDGVRGCDSYMVYLFDKSKT

VYEGPFASRSLSDCVNYIVQDSKIQLPIIQLRKVWAEAVHYVSGLKEDYSRLFQGQRA

AMLSLLRYNANLTKMKNTLISASQQLKAKLEFFHKSIQLDLERYSEQMTYGISSEKML

KAWKEMEEKAIHYAEVGVIGYLEDQIMSLHAEIMELQKSPYGRRQGDLMESLEQRAID

LYKQLKHRPSDHSYSDSTEMVKIIVHTVQSQDRVLKELFGHLSKLLGCKQKIIDLLPK

VEVALSNIKEADNTVMFMQGKRQKEIWHLLKIACTQSSARSLVGSSLEGAVTPQTSAW

LPPTSAEHDHSLSCVVTPQDGETSAQMIEENLNCLGHLSTIIHEANEEQGNSMMNLDW

SWLTE

FIG. 9

B. IKKα nucleotide sequence (GENBANK No. AF080157)

```
   1 cacgcgtccg cgagaaggag gactcgcaag cctcggcggc ccggaaccgg cctcggactg
  61 tcgacggaac ctgaggccgc ttgccctccc gccccatgga gcggcccccg gggctgcggc
 121 cgggcgcggg cgggccctgg gagatgcggg agcggctggg caccggcggc ttcgggaacg
 181 tctgtctgta ccagcatcgg gaacttgatc tcaaaatagc aattaagtct tgtcgcctag
 241 agctaagtac caaaaacaga gaacgatggt gccatgaaat ccagattatg aagaagttga
 301 accatgccaa tgttgtaaag gcctgtgatg ttcctgaaga attgaatatt ttgattcatg
 361 atgtgcctct tctagcaatg gaatactgtt ctggaggaga tctccgaaag ctgctcaaca
 421 aaccagaaaa ttgttgtgga cttaaagaaa gccagatact ttctttacta agtgatatag
 481 ggtctgggat tcgatatttg catgaaaaca aaattataca tcgagatcta aaacctgaaa
 541 acatagttct tcaggatgtt ggtggaaaga taatacataa aataattgat ctgggatatg
 601 ccaaagatgt tgatcaagga agtctgtgta catcttttgt gggaacactg cagtatctgg
 661 ccccagagct cttttgagaat aagccttaca cagccactgt tgattattgg agctttggga
 721 ccatggtatt tgaatgtatt gctggatata ggccttttt gcatcatctg cagccattta
 781 cctggcatga gaagattaag aagaaggatc caaagtgtat atttgcatgt gaagagatgt
 841 caggagaagt tcggtttagt agccatttac ctcaaccaaa tagcctttgt agtttaatag
 901 tagaacccat ggaaaactgg ctacagttga tgttgaattg ggaccctcag cagagaggag
 961 gacctgttga ccttactttg aagcagccaa gatgttttgt attaatggat cacattttga
1021 atttgaagat agtacacatc ctaaatatga cttctgcaaa gataatttct tttctgttac
1081 cacctgatga aagtcttcat tcactacagt ctcgtattga gcgtgaaact ggaataaata
1141 ctggttctca agaacttctt tcagagacag gaatttctct ggatcctcgg aaaccagcct
1201 ctcaatgtgt tctagatgga gttagaggct gtgatagcta tatggtttat ttgtttgata
1261 aaagtaaaac tgtatatgaa gggccatttg cttccagaag tttatctgat tgtgtaaatt
1321 atattgtaca ggacagcaaa atacagcttc caattataca gctgcgtaaa gtgtgggctg
1381 aagcagtgca ctatgtgtct ggactaaaag aagactatag caggctcttt cagggacaaa
1441 gggcagcaat gttaagtctt cttagatata atgctaactt aacaaaaatg aagaacactt
1501 tgatctcagc atcacaacaa ctgaaagcta aattggagtt ttttcacaaa agcattcagc
1561 ttgacttgga gagatacagc gagcagatga cgtatggggat atcttcagaa aaaatgctaa
1621 aagcatggaa agaaatggaa gaaaaggcca tccactatgc tgaggttggt gtcattggat
1681 acctggagga tcagattatg tctttgcatg ctgaaatcat ggagctacag aagagcccct
1741 atggaagacg tcaggagac ttgatggaat ctctggaaca gcgtgccatt gatctatata
1801 agcagttaaa acacagacct tcagatcact cctacagtga cagcacagag atggtgaaaa
1861 tcattgtgca cactgtgcag agtcaggacc gtgtgctcaa ggagctgttt ggtcatttga
1921 gcaagttgtt gggctgtaag cagaagatta ttgatctact ccctaaggtg gaagtggccc
1981 tcagtaatat caaagaagct gacaatactg tcatgttcat gcagggaaaa aggcagaaag
2041 aaatatggca tctccttaaa attgcctgta cacagagttc tgcccggtcc cttgtaggat
2101 ccagtctaga aggtgcagta accctcaga catcagcatg gctgcccccg acttcagcag
2161 aacatgatca ttctctgtca tgtgtggtaa ctcctcaaga tggggagact tcagcacaaa
2221 tgatagaaga aaatttgaac tgccttggcc atttaagcac tattattcat gaggcaaatg
2281 aggaacaggg caatagtatg atgaatcttg attggagttg gttaacagaa tgagttgtca
2341 cttgttcact gtccccaaac ctatggaagt tgttgctata catgttggaa atgtgttttt
2401 cccccatgaa accattcttc agacatcagt caatgaaga aatggctatg aacagaaact
2461 acatttctac tatgatcaga agaacatgat tttacaagta taacagtttt gagtaattca
2521 agcctctaaa cagacaggaa tttagaaaaa gtcaatgtac ttgtttgaat atttgtttta
2581 ataccacagc tatttagaag catcatcacg acacatttgc cttcagtctt ggtaaaacat
2641 tacttattta actgattaaa aataccttct atgtattagt gtcaactttt aacttttggg
2701 cgtaagacaa agtgtagttt tgtatacaga gaagaaaacc tcaagtaata ggcattttaa
2761 gtaaaagtct acctgtgttt ttttctaaaa aggctgctca caagttctat ttcttgaaga
2821 ataaattcta cctccttgtg ttgcactgaa caggttctct tcctggcatc ataaggagtt
```

FIG. 9B continued.

```
2881 ggtgtaatca ttttaaattc cactgaaaat ttaacagtat cccttctca tcgaagggat
2941 tgtgtatctg tgcttctaat attagttggc tttcataaat catgttgttg tgtgtatatg
3001 tatttaagat gtacatttaa taatatcaaa gagaagatgc ctgttaattt ataatgtatt
3061 tgaaaattac atgtttttc atttgtaaaa atgagtcatt tgtttaaaca atctttcatg
3121 tcttgtcata caaatttata aaggtctgca ctcctttatc tgtaattgta attccaaaat
3181 ccaaaaagct ctgaaaacaa ggtttccata agcttggtga caaaattcat ttgcttgcaa
3241 tctaatctga actgaccttg aatctttta tcccatttag tgtgaatatt cctttatttt
3301 gctgcttgat gatgagaggg agggctgctg ccacagactg tggtgagggc tggttaatgt
3361 agtatggtat atgcacaaaa ctactttct aaaatctaaa atttcataat tctgaaacaa
3421 cttgccccaa gggtttcaga gaaaggactg tggacctcta tcatctgcta agtaatttag
3481 aagatattat ttgtcttaaa aaatgtgaaa tgcttttata ttctaatagt ttttcacttt
3541 gtgtattaaa tggttttaa attaaaaaaa aaaaaaaaa
``` ing a compound to be screened, contacting said IKKα, said NIK and said compound, and detecting the transfer of said label to said IKKα.

SEQUENCE LISTING

<160> NUMBER OF SEQ ID NOS: 2

<210> SEQ ID NO 1
<211> LENGTH: 745
<212> TYPE: PRT
<213> ORGANISM: Homo sapiens

<400> SEQUENCE: 1

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45

```
Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
```

```
                465                 470                 475                 480
Glu Phe Phe His Lys Ser Ile Gln Leu Asp Leu Glu Arg Tyr Ser Glu
                    485                 490                 495
Gln Met Thr Tyr Gly Ile Ser Ser Glu Lys Met Leu Lys Ala Trp Lys
                    500                 505                 510
Glu Met Glu Glu Lys Ala Ile His Tyr Ala Glu Val Gly Val Ile Gly
                    515                 520                 525
Tyr Leu Glu Asp Gln Ile Met Ser Leu His Ala Glu Ile Met Glu Leu
                    530                 535                 540
Gln Lys Ser Pro Tyr Gly Arg Arg Gln Gly Asp Leu Met Glu Ser Leu
545                 550                 555                 560
Glu Gln Arg Ala Ile Asp Leu Tyr Lys Gln Leu Lys His Arg Pro Ser
                    565                 570                 575
Asp His Ser Tyr Ser Asp Ser Thr Glu Met Val Lys Ile Ile Val His
                    580                 585                 590
Thr Val Gln Ser Gln Asp Arg Val Leu Lys Glu Leu Phe Gly His Leu
                    595                 600                 605
Ser Lys Leu Leu Gly Cys Lys Gln Lys Ile Ile Asp Leu Leu Pro Lys
                    610                 615                 620
Val Glu Val Ala Leu Ser Asn Ile Lys Glu Ala Asp Asn Thr Val Met
625                 630                 635                 640
Phe Met Gln Gly Lys Arg Gln Lys Glu Ile Trp His Leu Leu Lys Ile
                    645                 650                 655
Ala Cys Thr Gln Ser Ser Ala Arg Ser Leu Val Gly Ser Ser Leu Glu
                    660                 665                 670
Gly Ala Val Thr Pro Gln Thr Ser Ala Trp Leu Pro Pro Thr Ser Ala
                    675                 680                 685
Glu His Asp His Ser Leu Ser Cys Val Val Thr Pro Gln Asp Gly Glu
                    690                 695                 700
Thr Ser Ala Gln Met Ile Glu Glu Asn Leu Asn Cys Leu Gly His Leu
705                 710                 715                 720
Ser Thr Ile Ile His Glu Ala Asn Glu Glu Gln Gly Asn Ser Met Met
                    725                 730                 735
Asn Leu Asp Trp Ser Trp Leu Thr Glu
                    740                 745

<210> SEQ ID NO 2
<211> LENGTH: 3579
<212> TYPE: DNA
<213> ORGANISM: Homo sapiens

<400> SEQUENCE: 2
cacgcgtccg cgagaaggag gactcgcaag cctcggcggc ccggaaccgg cctcggactg      60
tcgacggaac ctgaggccgc ttgccctccc gccccatgga gcggccccg gggctgcggc     120 cgggcgcggg cgggccctgg gagatgcggg agcggctggg caccggcggc ttcgggaacg     180
tctgtctgta ccagcatcgg gaacttgatc tcaaaatagc aattaagtct tgtcgcctag     240
agctaagtac caaaaacaga gaacgatggt gccatgaaat ccagattatg aagaagttga     300
accatgccaa tgttgtaaag gcctgtgatg ttcctgaaga attgaatatt ttgattcatg     360
atgtgcctct tctagcaatg gaatactgtt ctggaggaga tctccgaaag ctgctcaaca     420
aaccagaaaa ttgttgtgga cttaaagaaa gccagatact tcctttacta agtgatatag     480
ggtctgggat tcgatatttg catgaaaaca aaattataca tcgagatcta aaacctgaaa     540
```

-continued

```
acatagttct tcaggatgtt ggtggaaaga taatacataa aataattgat ctgggatatg     600
ccaaagatgt tgatcaagga agtctgtgta catcttttgt gggaacactg cagtatctgg     660
ccccagagct ctttgagaat aagccttaca cagccactgt tgattattgg agctttggga     720
ccatggtatt tgaatgtatt gctggatata ggcctttttt gcatcatctg cagccattta     780
cctggcatga aagattaag aagaaggatc caaagtgtat atttgcatgt gaagagatgt      840
caggagaagt tcggtttagt agccatttac ctcaaccaaa tagcctttgt agtttaatag     900
tagaacccat ggaaaactgg ctacagttga tgttgaattg ggaccctcag cagagaggag     960
gacctgttga ccttactttg aagcagccaa gatgttttgt attaatggat cacattttga    1020
atttgaagat agtacacatc ctaaatgtga cttctgcaaa gataatttct tttctgttac    1080
cacctgatga aagtcttcat tcactacagt ctcgtattga gcgtgaaact ggaataaata    1140
ctggttctca agaacttctt tcagagacag gaatttctct ggatcctcgg aaaccagcct    1200
ctcaatgtgt tctagatgga gttagaggct gtgatagcta tatggtttat ttgtttgata    1260
aaagtaaaac tgtatatgaa gggccatttg cttccagaag tttatctgat tgtgtaaatt    1320
atattgtaca ggacagcaaa atacagcttc aattataca gctgcgtaaa gtgtgggctg     1380
aagcagtgca ctatgtgtct ggactaaaag aagactatag caggctcttt cagggacaaa    1440
gggcagcaat gttaagtctt cttagatata atgctaactt aacaaaaatg aagaacactt    1500
tgatctcagc atcacaacaa ctgaaagcta aattggagtt ttttcacaaa agcattcagc    1560
ttgacttgga gagatacagc gagcagatga cgtatgggat atcttcagaa aaaatgctaa    1620
aagcatggaa agaaatggaa gaaaaggcca tccactatgc tgaggttggt gtcattggat    1680
acctggagga tcagattatg tctttgcatg ctgaaatcat ggagctacag aagagcccct    1740
atggaagacg tcagggagac ttgatggaat ctctggaaca gcgtgccatt gatctatata    1800
agcagttaaa acacagacct tcagatcact cctacagtga cagcacagag atggtgaaaa    1860
tcattgtgca cactgtgcag agtcaggacc gtgtgctcaa ggagctgttt ggtcatttga    1920
gcaagttgtt gggctgtaag cagaagatta ttgatctact ccctaaggtg gaagtggccc    1980
tcagtaatat caaagaagct gacaatactg tcatgttcat gcagggaaaa aggcagaaag    2040
aaatatggca tctccttaaa attgcctgta cacagagttc tgcccggtcc cttgtaggat    2100
ccagtctaga aggtgcagta acccctcaga catcagcatg gctgccccg acttcagcag     2160 aacatgatca ttctctgtca tgtgtggtaa ctcctcaaga tggggagact tcagcacaaa    2220
tgatagaaga aaatttgaac tgccttggcc atttaagcac tattattcat gaggcaaatg    2280
aggaacaggg caatagtatg atgaatcttg attggagttg gttaacagaa tgagttgtca    2340
cttgttcact gtccccaaac ctatggaagt tgttgctata catgttggaa atgtgttttt    2400
cccccatgaa accattcttc agacatcagt caatggaaga aatggctatg aacagaaact    2460
acatttctac tatgatcaga agaacatgat tttacaagta taacagtttt gagtaattca    2520
agcctctaaa cagacaggaa tttagaaaaa gtcaatgtac ttgtttgaat atttgtttta    2580
ataccacagc tatttagaag catcatcacg acacatttgc cttcagtctt ggtaaaacat    2640
tacttattta actgattaaa aataccttct atgtattagt gtcaactttt aacttttggg    2700
cgtaagacaa agtgtagttt tgtatacaga gaagaaaacc tcaagtaata ggcattttaa    2760
gtaaaagtct acctgtgttt ttttctaaaa aggctgctca caagttctat ttcttgaaga    2820
ataaattcta cctccttgtg ttgcactgaa caggttctct tcctggcatc ataaggagtt    2880
ggtgtaatca tttaaattc cactgaaaat ttaacagtat ccccttctca tcgaagggat     2940
```

-continued

```
tgtgtatctg tgcttctaat attagttggc tttcataaat catgttgttg tgtgtatatg    3000
tatttaagat gtacatttaa taatatcaaa gagaagatgc ctgttaattt ataatgtatt    3060
tgaaaattac atgtttttc atttgtaaaa atgagtcatt tgtttaaaca atctttcatg     3120
tcttgtcata caaatttata aaggtctgca ctcctttatc tgtaattgta attccaaaat    3180
ccaaaaagct ctgaaaacaa ggtttccata agcttggtga caaaattcat ttgcttgcaa    3240
tctaatctga actgaccttg aatctttta tcccatttag tgtgaatatt cctttatttt     3300
gctgcttgat gatgagaggg agggctgctg ccacagactg tggtgagggc tggttaatgt    3360
agtatggtat atgcacaaaa ctacttttct aaaatctaaa atttcataat tctgaaacaa    3420
cttgccccaa gggtttcaga gaaaggactg tggacctcta tcatctgcta agtaatttag    3480
aagatattat ttgtcttaaa aaatgtgaaa tgctttata ttctaatagt ttttcacttt     3540
gtgtattaaa tggtttttaa attaaaaaaa aaaaaaaa                            3579
```

INHIBITION OF B-CELL MATURATION AND ANTIBODY PRODUCTION

This application is a continuation of U.S. application Ser. No. 10/176,789, filed on Jun. 21, 2002 now abandoned, which claims priority to provisional application Ser. No. 60/300,109, filed Jun. 21, 2001, hereby incorporated by reference in their entirety.

This invention was made, in part, with Government support by the National Institutes of Health Grant Numbers AI43477 and ES04151, and the American Cancer Society Grant Number 110-01. Therefore, the Government may have certain rights in the invention.

FIELD OF THE INVENTION

The present invention provides methods and compositions for the inhibition of B-cell maturation and antibody production without interfering with innate or T-cell mediated immunity.

BACKGROUND OF THE INVENTION

The immune system has evolved to protect animals from pathogens. The cells which mediate immunity include lymphocytes and phagocytes. Lymphocytes recognize antigens on pathogens, and phagocytes internalize pathogens and degrade them. An immune response consists of two phases: In the first phase, an antigen activates specific lymphocytes whose receptors recognize it; in the second phase, the effector phase, the activated lymphocytes coordinate an immune response that eliminates the source of the antigens. Lymphocytes consist of different cells with specialized functions. B cells make antibodies, which recognize and bind to antigens; cytotoxic T cells kill virally infected cells; Helper T cells coordinate the immune response by direct cell-cell interactions and the release of cytokines, which help B cells make antibody; and macrophages kill parasites that have invaded them. B cells usually recognize intact antigen molecules, while T lymphocytes recognize antigen fragments on the surface of other cells.

All lymphocytes are derived from bone-marrow stem cells, but T cells develop in the thymus, while B cells develop in the bone marrow. B cells differentiate from lymphoid cells into virgin B cells, and then may be driven by antigen to become memory cells or plasma cells. The genes coding for antibody are rearranged during the course of B cell development. B-cell maturation and differentiation is an ordered and complex process that ultimately results in the expression of antibodies (i.e., immunoglobulins, or Igs). Antibodies are extremely important components of the immune system, due to their recognition of and binding to antigens, as well as to their involvement in the initiation of various biologic processes that are independent of antibody specificity However, the immune system may break down; this can lead to immunodeficiency or hypersensitivity diseases, or to autoimmune diseases. Immunodeficiency results when any elements of the immune system are defective, resulting in an inability to fight infections adequately. Some immunodeficiencies are genetic, while others, such as AIDS, are acquired. Hypersensitivity results from immune reactions which are disproportionate to the damage that could be caused by a pathogen, or where the immune system mounts a reaction to a harmless antigen, such as a food molecule. In a hypersensitivity response, the immune reaction may cause more damage than the pathogen or antigen. Examples of hypersensitivity include hay fever and asthma. Autoimmunity results from an inappropriate reaction to self antigens. The immune system normally recognizes all foreign antigens and reacts against them, while recognizing the body's own tissues as "self;" however, in autoimmunity, the system reacts against self components. Examples of autoimmune diseases include rheumatoid arthritis and pernicious anaemia.

One source of immune system breakdown is the complexity of the development and interactions of the different components if the immune system. As the pathway of B-cell development is complicated and involves numerous factors and interactions, there are many opportunities for errors and/or abnormal development. As noted above, one such set of errors is the loss of tolerance of "self," with the resultant production of autoimmune disease. In addition, various leukemias (e.g., chronic lymphocytic leukemia) and other malignant conditions may arise during abnormal B-cell development. Thus, there is a need to prevent abnormal B-cell development and/or activation. To date, current methods to prevent abnormal B-cell development and/or activation appear to adversely impact innate and/or T-cell mediated (i.e., cell-mediated) immunity. Thus, there is also a need to prevent abnormal B-cell development without interfering with innate or T-cell mediated immune function.

SUMMARY OF THE INVENTION

The present invention provides methods and compositions for the inhibition of B-cell maturation and antibody production without interfering with innate or T-cell mediated immunity.

In particular, the present invention also provides methods for the use of IKKα for the specific inhibition of B-cell maturation and antibody production without interfering with innate immunity or T-cell mediated immunity. Thus, the present invention finds use in prevention of diseases associated with antibody-mediated pathology, including but not limited to graft rejection, graft vs. host disease, and autoimmune disease. In addition, the present invention provides means to inhibit the proliferation of B-cell tumors, such as multiple myeloma and chronic lymphocytic leukemia.

Thus, the present invention provides methods of screening compounds which reduce phosphorylation of IKKα. In some embodiments, the method comprises providing IKKα, NIK, and a compound to be screened, contacting the IKKα, the NIK and the compound, and detecting a reduced level of phosphorylation of IKKα by NIK in the presence of the compound, thereby identifying the test compound as reducing phosphorylation of IKKα.

In other embodiments, the method comprises providing a first composition comprising IKKα, NIK, and a compound to be screened, providing a second composition comprising NIK, the compound to be screened, and IKKα which contains alanine at an amino acid position selected from the group consisting of 1) position 176, 2) position 180, and 3) positions 176 and 180, and detecting a reduced level of phosphorylated IKKα in the first composition compared to the second composition, thereby identifying the compound as reducing phosphorylation of IKKα.

The present invention also provides compositions comprising a mouse cell expressing IKKα that contains alanine at an amino acid position selected from the group consisting of 1) position 176, 2) position 180, and 3) positions 176 and 180.

The present invention also provides methods to screen compounds that inhibit phosphorylation of IKKα. In some embodiments, the method comprises providing a composition comprising IKKα, NIK, a labeled phosphorylation source such that the label is transferred to IKKα by NIK, and a compound to be screened, and detecting phosphorylated IKKα under conditions sufficient to detect inhibition of phosphorylation of IKKα. In other embodiments, the compound prevents phosphorylation of IKKα at amino acid serine at position 176, of amino acid serine at position 180, or at both amino acid serine at position 176 and amino acid serine at position 180.

In other embodiments, the method to screen compounds that inhibit phosphorylation of IKKα comprise providing a first composition comprising IKKα, NIK, a labeled phosphorylation source such that the label is transferred to IKKα by NIK, and a compound to be screened, and a second composition comprising a modified IKKα, NIK, a phosphorylation source, and the compound to be screened, wherein the modified IKKα is an altered form which is not phosphorylated, detecting phosphorylated IKKα in the first composition and detecting phosphorylated modified IKKα in the second composition, and comparing the amount of phosphorylated IKKα in the first composition and the amount of phosphorylated modified IKKα in the second composition, thereby detecting inhibition of phosphorylation of IKKα. In particular embodiments, the modified IKKα comprises at least one substitute amino acid which is not phosphorylated. In further particular embodiments, the at least one substitute amino acid is present at amino acid position 176, at amino acid position 180, or at both amino acid position 176 and amino acid position 180. In further particular embodiments, the at least one substitute amino acid is alanine.

The present invention also provides methods to screen compounds which inhibit processing of p100 (:RelB) via phosphorylated IKKα. In some embodiments, the method comprises providing a composition comprising IKKα, NIK, a labeled phosphorylation source such that the label is transferred to IKKα by NIK, and a compound to be screened, and detecting phosphorylated IKKα, under conditions sufficient to detect inhibition of phosphorylation of IKKα. In some further embodiments, the compound prevents phosphorylation of IKKα at amino acid serine at position 176, of amino acid serine at position 180, or of both amino acid serine at position 176 and amino acid serine at position 180. In other embodiments, the method to screen compounds which inhibit processing of p100 (:RelB) via phosphorylated IKKα comprises providing a first composition comprising IKKα, NIK, a labeled phosphorylation source such that the label is transferred to IKKα by NIK, and a compound to be screened, and a second composition comprising a modified IKKα, NIK, a labeled phosphorylation source such that the label is transferred to IKKα by NIK, and the compound to be screened, wherein the modified IKKα is an altered form which is not phosphorylated, detecting phosphorylated IKKα in the first composition and detecting phosphorylated modified IKKα in the second composition, and comparing the amount of phosphorylated IKKα in the first composition and the amount of phosphorylated modified IKKα in the second composition, thereby detecting inhibition of phosphorylation of IKKα and compounds which inhibit processing of p100 (:RelB) via phosphorylated IKKα. In some further embodiments, the modified IKKα comprises at least one substitute amino acid that is not phosphorylated. In yet some further embodiments, the at least one substitute amino acid is present at amino acid position 176, at amino acid position 180, or at both amino acid position 176 and amino acid position 180. In yet some further embodiments, the at least one substitute amino acid is alanine.

The present invention also provides compositions. In some embodiments, the composition comprises a mouse cell expressing a modified IKKα, wherein the modified IKKα is not phosphorylated. In some further embodiments, the cell is prepared by knocking out endogenous IKKα and knocking in the modified IKKα. In some further embodiments, the modified IKKα comprises at least one substitute amino acid that is not phosphorylated. In some further embodiments, the at least one substitute amino acid is present at amino acid position 176, at amino acid position 180, or at both amino acid position 176 and amino acid position 180. In yet some further embodiments, the at least one substitute amino acid is alanine.

The present invention also provides methods to screen compounds which inhibit phosphorylation of wild-type IKKα. In some embodiments, the method comprises providing a first composition comprising a mouse cell comprising wild-type IKKα, a labeled phosphorylation source such that the label is transferred to IKKα by NIK and a compound to be screened, and a second composition comprising a mouse cell comprising a modified IKKα, wherein the modified IKKα is not phosphorylated, a labeled phosphorylation source such that the label is transferred to IKKα by NIK and the compound to be screened, detecting phosphorylated wild-type IKKα in the first composition and detecting phosphorylated modified IKKα in the second composition, and comparing the amount of phosphorylated wild-type IKKα in the first composition and of phosphorylated modified IKKα in the second composition, thereby detecting inhibition of phosphorylation of wild type IKKα.

The present invention also provides methods to screen compounds which inhibit processing of p100 (:RelB) via phosphorylated IKKα. In some embodiments, the method comprises providing a first composition comprising a mouse cell comprising wild-type IKKα and a compound to be screened, and detecting an amount of processed p100 (:RelB) in the mouse cell, thereby detecting inhibition of processing p100 (:RelB).

In other embodiments, a method to screen compounds which inhibit processing of p100 (:RelB) via phosphorylated IKKα comprises providing a first composition comprising a mouse cell comprising wild-type IKKα and a compound to be screened, and a second composition comprising a mouse cell comprising a modified IKKα, wherein the modified IKKα is not phosphorylated, and the compound to be screened, detecting an amount of processed p100 (:RelB) in the mouse cell comprising wild-type IKKα and detecting an amount of processed p100 (:RelB) in the mouse cell comprising a modified IKKα, wherein the modified IKKα is not phosphorylated, and comparing the amount of processed p100 (:RelB) in the mouse cell comprising wild-type IKKα with the amount of processed p100 (:RelB) in the mouse cell comprising a modified IKKα, thereby detecting inhibition of processing p100 (:RelB).

The present invention also provides a method of reducing the severity of a pathological condition associated with antibody production or B cell maturation in an individual, comprising administering to the individual an agent that reduces phosphorylation of IKKα. In some embodiments, the pathological condition is associated with antibody production and is selected from the group consisting of transplantation rejection and autoimmune disease. In other embodiments, the pathological condition is leukemia. In yet other embodiments, the individual is a human. In other embodiments, the agent is administered intravenously; in yet other embodiments, the agent is administered orally; and in yet other embodiments, the agent is administered into a neoplasm.

The present invention also provides methods of reducing maturation of a B cell or of inhibiting antibody production, or of both, comprising reducing phosphorylation of IKKα in the B cell. In some embodiments, the method comprises knocking out the nucleic acid sequence encoding IKKα in the B cell, and replacing the knocked out nucleic acid sequence encoding IKKα with a nucleotide sequence encoding an IKKα amino acid sequence which contains an alanine at amino positions amino acid 176, at amino acid position 180, or at both positions. In some embodiments, the B cell is in a mammal. In further embodiments, T-cell mediated immunity in the mammal is not reduced. In yet additional further embodiments, innate immunity in said mammal is not reduced. In yet additional further embodiments, the mammal has a pathological condition associated with antibody production, where the pathology is a transplantation rejection or an autoimmune disease. In other additional further embodiments, the mammal has leukemia.

The present invention also provides methods of identifying a compound which reduces phosphorylation of IKKα. In some embodiments, the method comprises providing IKKα, NIK, and a compound, contacting the IKKα, the NIK and the compound, and detecting a reduced level of phosphorylation of IKKα in the presence of the compound, thererby identifying the test compound as reducing phosphorylation of IKKα. In some embodiments, the IKKα is in a B cell. In other embodiments, instead of detecting a reduced level of phosphorylation of IKKα in the presence of the compound, the method comprises detecting a reduced level of maturation of the B cells in the presence of the compound, thereby identifying the test compound as reducing phosphorylation of IKKα. In other embodiments, the B cells produce an antibody, and instead of detecting a reduced level of phosphorylation of IKKα in the presence of the compound, the method comprises detecting a reduced level of the antibody produced by B cells in the presence of the compound, thereby identifying the test compound as reducing phophorylation of IKKα in B cells.

DESCRIPTION OF THE FIGURES

FIG. 7 provides a Table showing the results of an analysis of NF-κB target gene expression in wild-type and Ikkα$^{AA}$ B cells. Wild-type and Ikkα$^{AA}$ mice were injected with LPS (i.p., 5 mg/kg) or PBS. After 1 hour and 4 hours, splenic B cells were isolated and their RNA extracted. The expression of the indicated NF-κB target genes was analyzed by Real-Time PCR (TaqMan, PE Applied Biosystems) and normalized to the level of cyclophilin mRNA as known in the art (See e.g., Gibson et al., Genome Res., 6:995 [1996]). Reverse transcription was performed using 2 μg of total RNA. PCR included a denaturation step at 95 C for 15 seconds and 60 C for 1 minute. The values shown in this Table represent fold change in mRNA abundance relative to the untreated sample of each genotype and are averages of two fully separate experiments.

FIG. 9 shows the amino acid sequence of IKKα (SEQ ID NO:1, panel A) and the nucleotide sequence of IKKα (SEQ ID NO:2, panel B).

DEFINITIONS

Figure 1:
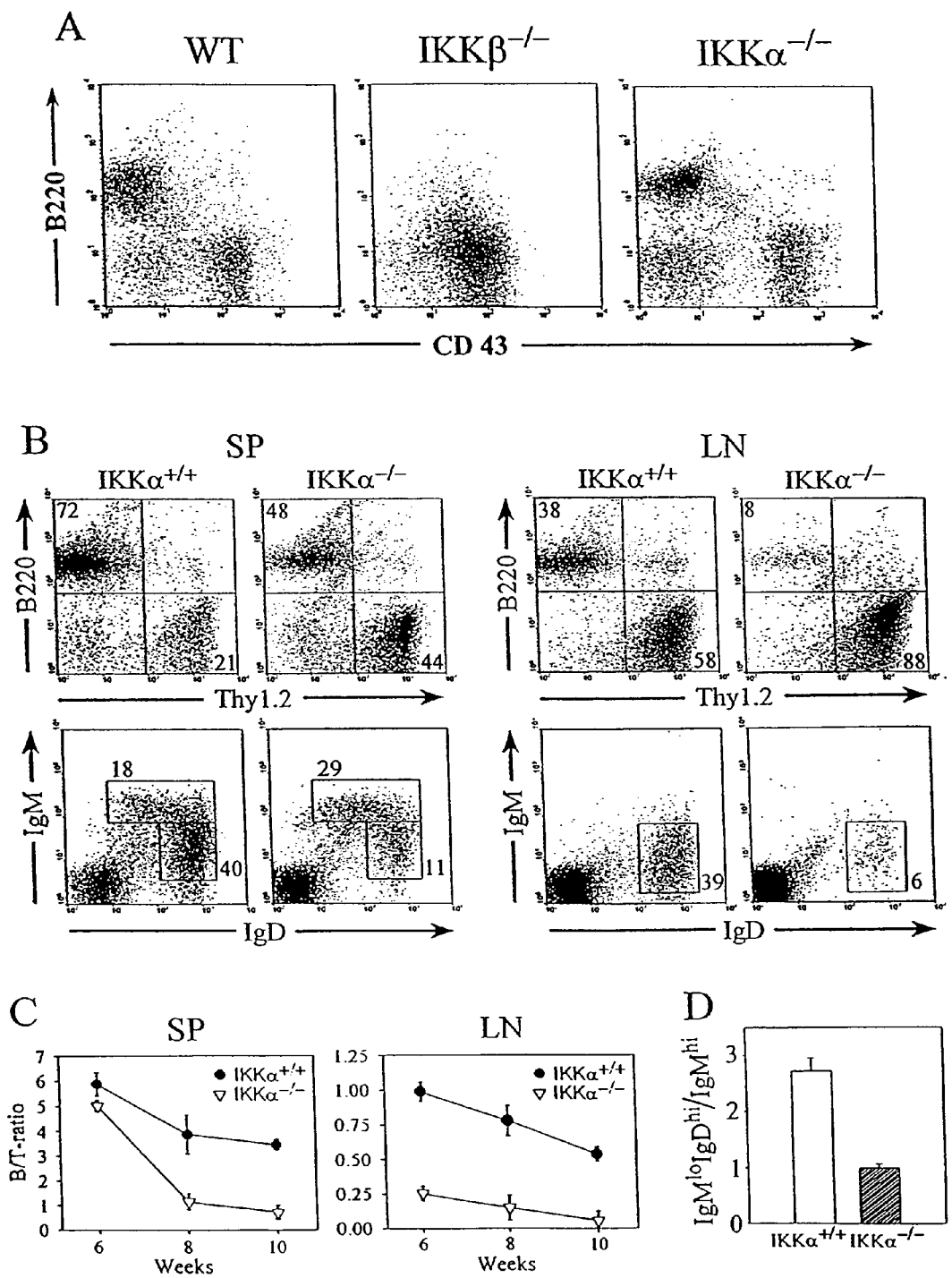
FIG. 1 provides data for defective B-cell maturation in Ikkα$^{-/-}$ radiation chimeras (i.e., normal mice whose hematopoietic system was reconstituted with Ikk-deficient stem cells). Panel A provides flow cytometric analysis of CD45.2 (donor derived) cells 6 weeks after engraftment of lethally irradiated mice with either wt, Ikkα$^{-/-}$, or Ikkβ$^{-/-}$ FL stem cells. B220 is a marker specific for B lymphoid (B220) and CD43 marks all hematopoietic cells except erythroid and resting B cells. Data are representative of at least 4 mice per group. Panel B provides data for splenocytes (SP) and lymph node (LN) cells of wt (Ikkα$^{+/+}$) and Ikkα$^{-/-}$ radiation chimeras analyzed for the expression of B-cell (B220, IgM, IgD) and T-cell (Thy1.2) markers. Percentages of positive cells in indicated regions are shown. Dot plots are representative of 6 independent experiments. Panel C provides the B-cell to T-cell ratio at 6, 8, and 10 weeks post-engraftment in spleen (SP) and lymph nodes (LN), based on the percentages of B220$^+$ and Thy1.2 cells (mean±SD, n=3, each group). Panel D provides the ratio of IgM$^{lo}$IgD$^{hi}$ to IgM$^{hi}$ B-cells 8 weeks after reconstitution (mean±SD, n=3, each group).

To facilitate an understanding of the invention, a number of terms are defined below.

As used herein, the term "lymphocyte" refers to cells at a specific stage in the T or B cell lineage, while the term "lymphoid" is used to denote the entire lineages (i.e., encompassing cells at all developmental stages) or tissues in which cells from these lineages normally predominate.

As used herein, the term "lymphoid cells" refers to the various lymphocytes, including T-cells, B-cells, and natural killer (NK) cells.

As used herein, the term "B-cell" refers to lymphocytes that are capable of producing antibodies. These cells are the primary cell type involved in humoral acquired immunity.

As used herein, the term "T-cell" refers to lymphocytes that do not produce antibodies. These cells are the primary cell type involved in cell-mediated acquired immunity.

As used herein, the terms "phagocytic cells" and "phagocytes" refer to monocytes, macrophages and polymorphonuclear granulocytes (i.e., neutrophils, eosinophils, and basophils).

As used herein, the term "antigen-presenting cell" refers to cells that are required by T-cells to enable them to respond to antigens.

As used herein, the term "NF-κB" refers to Nuclear factor kappa B, which is a transcription factor. NF-κB2 is synthesized as a large precursor, p100, which requires proteolytic processing to produce the p52 NF-κB subunit.

As used herein, the term "IKKα" refers to one of two catalytic subunits of IKK, where the other catalytic subunit is IKKβ.

As used herein, the term "NIK" refers to NF-γB inducing kinase.

As used herein, the term "phosphorylation source" refers to a source of a phosphate group that can be transferred by a kinase from the source to an acceptor. In the context of the present invention, the phosphorylation source provides a phosphate group which can be transferred to IKKα; it is contemplated that the kinase is NIK. Exemplary phosphorylation sources include but are not limited to ATP, GTP, and high energy phosphate compounds capable of donating a phosphate group to an acceptor via a kinase.

As used herein, the terms "reducing phosphorylation of IKKα" when made in reference to the effect of an agent means that the agent reduces the level of phosphorylation of IKKα to a quantity which is preferably 10% less than, more preferably 50% less than, yet more preferably 75% than, even more preferably 90% less than, the quantity of phosphorylation in a corresponding control sample, and most preferably is at the same level which is observed in a control sample. A reduced level of phosphorylation of IKKα need not, although it may, mean an absolute absence of phosphorylation of IKKα. The invention does not require, and is not limited to, methods which wholly eliminate phosphorylation of IKKα. The terms "reducing," "inhibiting," and "preventing" are used interchangeably.

As used herein, the term "agent" means a molecule that can reduce phosphorylation of IKKα. The term "compound" when used in reference to a molecule that can reduce phosphorylation of IKKα is used interchangeably with the term "agent."

As used herein, the terms "reducing the level of expression of IKKα" "diminishing IKKα expression" and grammatical equivalents thereof refer to reducing the level of IKKα expression to a quantity which is preferably 20% less than the quantity in a corresponding control tissue, more preferably is 50% less than the quantity in a corresponding control tissue, yet more preferably is 90% less than the quantity in a corresponding control tissue, and most preferably is at the background level of, or is undetectable by, a Western blot analysis of IKKα, by immunofluorescence for detection of IKKα, by reverse transcription polymerase chain (RT-PCR) reaction for detection of IKKα mRNA, or by in situ hybridization for detection of IKKα mRNA. When a background level or undetectable level of IKKα peptide or mRNA is measured, this may indicate that IKKα is not expressed. A reduced level of IKKα polypeptide or mRNA need not, although it may, mean an absolute absence of expression of IKKα. The invention does not require, and is not limited to, antisense IKKα sequences which eliminate expression of IKKα.

As used herein, the term "ribozyme" refers to an RNA sequence that hybridizes to a complementary sequence in a substrate RNA and cleaves the substrate RNA in a sequence specific manner at a substrate cleavage site. Typically, a ribozyme contains a "catalytic region" flanked by two "binding regions." The ribozyme binding regions hybridize to the substrate RNA, while the catalytic region cleaves the substrate RNA at a "substrate cleavage site" to yield a "cleaved RNA product." The nucleotide sequence of the ribozyme binding regions may be completely complementary or partially complementary to the substrate RNA sequence with which the ribozyme binding regions hybridize. Complete complementarity is preferred in order to increase the specificity, as well as the turnover rate (i.e., the rate of release of the ribozyme from the cleaved RNA product), of the ribozyme. Partial complementarity, while less preferred, may be used to design a ribozyme binding region containing more than about 10 nucleotides. While contemplated to be within the scope of the claimed invention, partial complementarity is generally less preferred than complete complementarity since a binding region having partial complementarity to a substrate RNA exhibits reduced specificity and turnover rate of the ribozyme when compared to the specificity and turnover rate of a ribozyme which contains a binding region having complete complementarity to the substrate RNA. A ribozyme may hybridize to a partially or completely complementary DNA sequence but cannot cleave the hybridized DNA sequence since ribozyme cleavage requires a 2'-OH on the target molecule, which is not available on DNA sequences.

As used herein, the term "primary lymphoid organs" (i.e., "primary lymph organs") refers to the major sites of lymphocyte development. It is in these sites that lymphocytes differentiate from lymphoid stem cells, proliferate, and mature into functional cells. In mammals, T-cells mature in the thymus, while B-cells mature in the bone marrow. In birds, the bursa of Fabricius is a specialized site for B-cell maturation. It is in the primary lymphoid organs that lymphocytes acquire their initial repertoire of specific antigen receptors, and cells are selected for autotolerance (i.e., so that they are only capable of recognizing non-self antigens). In addition to being a site of B-cell development, the post-natal bone marrow contains mature T-cells and plasma cells. These organs are also the site where T-cells "learn" to recognize self MHC (major histocompatibility) molecules. There is some evidence that some lymphocyte development occurs outside the primary lymphoid organs, such as in germinal centers within the spleen. These sites are primarily responsible for the maturation of B-cells and T-cells. However, as the post-natal bone marrow contains mature T-cells and plasma cells it also functions as an important secondary lymphoid organ in humans.

As used herein, the terms "secondary lymph organs" (i.e., secondary lymphoid organs) and "secondary lymph tissues" (i.e., secondary lymphoid tissues) refer to the spleen, lymph nodes, mucosa-associated lymphoid tissues (MALT), including the tonsils and Peyer's patches. However, the MALT is not limited to these particular sites, as the term encompasses all lymphoid tissues associated with the mucosae (e.g., Waldeyer's ring, bronchus-associated lymphoid tissue, lymphoid nodules, and urogential tissue). Following their generation in the primary lymphoid tissues, lymphocytes migrate into the peripheral secondary lymphoid tissues. These tissues provide an environment in which lymphocytes can interact with antigens, each other and accessory cells. In general, immune responses generated in these secondary lymphoid tissues require phagocytic macrophages, antigen-presenting cells, stromal cells, mature T-cells, and mature B-cells.

As used herein, the term "antibody" or "antibodies" refers to any immunoglobulin that binds specifically to an antigenic determinant, and specifically, binds to proteins identical or structurally related to the antigenic determinant which stimulated its production. Thus, antibodies can be used to detect the antigen which stimulated their production. Monoclonal antibodies are derived from a single clone of B lymphocytes (i.e., B cells), and are homogeneous in structure and antigen specificity. Polyclonal antibodies originate from many different clones of antibody-producing cells, and thus are heterogenous in their structure and epitope specificity, but in a population of polyclonals given the same designation, are all directed to the same molecule. Monoclonal and polyclonal antibodies may or may not be purified. For example, polyclonal antibodies contained in crude antiserum may be used in this unpurified state. It is intended that the term "antibody" encompass any immunoglobulin (e.g., IgG, IgM, IgA, IgE, IgD, etc.) obtained from any source (e.g., humans, rodents, non-human primates, caprines, bovines, equines, ovines, etc.).

The terms "specific binding" or specifically binding" when used in reference to the interaction of an antibody and a protein or peptide means that the interaction is dependent upon the presence of a particular structure (i.e., the antigenic determinant or epitope) on the protein. In other words, the antibody recognizes and binds to a specific protein structure rather than to proteins in general.

As used herein, the term "antigen" is used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen or portion of an antigen.

The terms "antigenic determinant" and "epitope" as used herein, refer to that portion of an antigen that makes contact with a particular antibody variable region. When a protein or fragment of a protein is used to immunize a host animal, numerous regions of the protein may induce the production of antibodies which bind specifically to a given region or three-dimensional structure on the protein; these regions or structures are referred to as antigenic determinants.

As used herein, the term "subject" refers to any animal, including humans.

As used herein, the term "animal" refers to any animal, including humans, as well as vertebrates such as rodents, non-human primates, ovines, bovines, ruminants, lagomorphs, porcines, caprines, equines, canines, felines, aves, etc.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia.

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease, from sub-clinical infection to full-blown disease, wherein the subject exhibits at least some of the indicia (e.g., signs and symptoms) associated with the particular disease.

As used herein, the term "disease" refers to any pathological condition, and encompasses infectious diseases, cancer, and other abnormalities. Indeed, it is not intended that the present invention be limited to any particular disease. In addition, the term encompasses the signs and symptoms associated with pathological processes (e.g., the indicators of inflammation). In particularly preferred embodiments, the subject of interest is experiencing skin pathology, including but not limited to wound(s), cancer or other malignancies, congenital defects, etc. In alternative embodiments, the subject is experiencing cosmetic flaws and/or abnormalities.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "wild-type" refers to a gene or gene product which has the characteristics of that gene or gene product when isolated from a naturally occurring source. A wild-type gene is that which is most frequently observed in a population and is thus arbitrarily designated as the "normal" or "wild-type" form of the gene. In contrast, the term "modified" (or "mutant") refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "nucleotide encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, etc. or a combination of both endogenous and exogenous control elements.

Transcriptional control signals in eukaryotes comprise "enhancer" elements. Enhancers consist of short arrays of DNA sequences that interact specifically with cellular proteins involved in transcription (Maniatis et al., Science 236: 1237 [1987]). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual,* 2nd ed., Cold Spring Harbor Laboratory Press, New York, pp. 16.7-16.8 [1989]). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "promoter," "promoter element," or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

A transformed cell is a cell or cell line that has acquired the ability to grow in cell culture for many multiple generations, the ability to grow in soft agar and the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

The term "cloning" as used herein, refers to the process of isolating a nucleotide sequence from a nucleotide library, cell or organism for replication by recombinant techniques.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

The term "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Amino acid sequence," "polypeptide sequence," peptide sequence, and peptide are used interchangeably herein to refer to a sequence of amino acids.

"Nucleic acid sequence," "nucleotide sequence," and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

As used herein, the terms oligonucleotides and oligomers refer to a nucleic acid sequence of at least about 10 nucleotides and as many as about 60 nucleotides, preferably about 15 to 30 nucleotides, and more preferably about 20-25 nucleotides, which can be used as a probe or amplimer.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and of non-coding regulatory sequences that do not encode an mRNA or protein product (e.g., promoter sequence, enhancer sequence, polyadenylation sequence, termination sequence, etc.).

The term "portion" when used in reference to a nucleotide sequence refers to fragments of that nucleotide sequence. The fragments may range in size from 5 nucleotide residues to the entire nucleotide sequence minus one nucleic acid residue. The term "portion" when used in reference to an amino acid sequence refers to fragments of the amino acid sequence. The fragments may range in size from 3 amino acids to the entire amino acid sequence minus one amino acid residue.

An oligonucleotide sequence which is a "homolog" of a first nucleotide sequence is defined herein as an oligonucleotide sequence which exhibits greater than or equal to 50% identity, and more preferably greater than or equal to 70% identity, to the first nucleotide sequence when sequences having a length of 10 bp or larger are compared.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary (i.e., "substantially homologous") to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ C to about 20 C to 25 C below $T_m$. As will be understood by those of skill in the art, a stringent hybridization can be used to identify or detect identical polynucleotide sequences or to identify or detect similar or related polynucleotide sequences. Under "stringent conditions" the nucleotide sequence portions thereof, will hybridize to its exact complement and closely related sequences.

Low stringency conditions comprise conditions equivalent to binding or hybridization at 68 C in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 2.0×SSPE, 0.1% SDS at room temperature when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5× Denhardt's reagent and 100 µg/ml denatured salmon sperm DNA followed by washing in a solution comprising 0.1×SSPE and 0.1% SDS at 68° C. when a probe of about 100 to about 1000 nucleotides in length is employed.

When used in reference to a double-stranded nucleic acid sequence such as a cDNA or genomic clone, the term "substantially homologous" refers to any probe which can hybridize either partially or completely to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations which take structural as well as sequence characteristics into account for the calculation of $T_m$.

"Amplification" is defined herein as the production of additional copies of a nucleic acid sequence and is generally carried out using polymerase chain reaction technologies well known in the art (See e.g., Dieffenbach and Dveksler, *PCR Primers a Laboratory Manual*, Cold Spring Harbor Press, Plainview N.Y. [1995]). As used herein, the term "polymerase chain reaction" ("PCR") refers to the methods of U.S. Pat. Nos. 4,683,195, 4,683,202, and 4,965,188, all of which are hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded DNA at or near a specific nucleotide sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extra-chromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the terms "purified," "to purify," and "purification" refer to the removal or reduction of at least one contaminant from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample (i.e., "enrichment" of an antibody).

The terms "Western blot," "Western immunoblot," "immunoblot," and "Western" refer to the immunological analysis of protein(s), polypeptides or peptides that have been immobilized onto a membrane support. The proteins are first resolved by acrylamide gel electrophoresis to separate the proteins, followed by transfer of the proteins from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody which specifically binds the primary antibody. The secondary antibody is typically conjugated to an enzyme which permits visualization by the production of a colored reaction product or catalyzes a luminescent enzymatic reaction (e.g., ECL reagent, Amersham).

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (See, Sambrook et al., *Molecular Cloning: A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size, followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, J. et al., supra, pp 7.39-7.52 [1989]).

As used herein, the term "ELISA" refers to enzyme-linked immunosorbent assay. Numerous methods and applications for carrying out an ELISA are well known in the art, and provided in many sources (See e.g., Crowther, "Enzyme-Linked Immunosorbent Assay (ELISA)," in *Molecular Biomethods Handbook*, Rapley et al. [eds.], pp. 595-617, Humana Press, Inc., Totowa, N.J. [1998]; Harlow and Lane (eds.), *Antibodies: A Laboratory Manual*, Cold Spring Harbor Laboratory Press [1988]; and Ausubel et al. (eds.), *Current Protocols in Molecular Biology*, Ch. 11, John Wiley & Sons, Inc., New York [1994]).

As used herein, the term "in vitro" refers to an artificial environment and to processes or reactions that occur within an artificial environment. In vitro environments consist of, but are not limited to, controlled laboratory conditions. The term "in vivo" refers to the natural environment (e.g., within an organism or a cell) and to processes or reactions that occur within that natural environment.

The terms "sample" and "specimen" are used in their broadest sense and encompass samples or specimens obtained from any source. As used herein, the term "biological samples" refers to samples or specimens obtained from animals (including humans), and encompasses cells, fluids, solids, tissues, and gases. In preferred embodiments of this invention, biological samples include tissues (e.g., biopsy material), cerebrospinal fluid (CSF), serous fluid, blood, and blood products such as plasma, serum and the like. However, these examples are not to be construed as limiting the types of samples which find use with the present invention.

As used herein, the term "kit" is used in reference to a combination of reagents and other materials. It is contemplated that the kit may include reagents such as antibodies, control proteins, as well as testing containers (e.g., microtiter plates, etc.). It is not intended that the term "kit" be limited to a particular combination of reagents and/or other materials.

DESCRIPTION OF THE INVENTION

The present invention provides methods and compositions for the inhibition of B-cell maturation and antibody production without interfering with innate or T-cell mediated immunity.

In particular, the present invention also provides methods for the use of IKKα for the specific inhibition of B-cell maturation and antibody production without interfering with innate immunity or T-cell mediated immunity. Thus, the present invention finds use in prevention and/or treatment of pathologies of B cell or antibody origin. Diseases associated with antibody-mediated pathology include but not limited to graft rejection, graft vs. host disease, and autoimmune disease. In addition, the present invention finds use in inhibition of the proliferation of B-cell tumors, including but not limited to multiple myeloma and chronic lymphocytic leukemia.

The invention is based upon the inventor's discovery of a specific signaling pathway that that is specifically required for maturation of B cells and for production of secondary lymphoid organs, where the pathway is amenable to inhibition. Inhibition or interference with this pathway is contemplated to prevent all antibody-mediated pathologies, including graft rejection, graft vs. host disease and autoimmune diseases. In addition, interference with this pathway is contemplated to inhibit the proliferation of certain B cell tumors, such as multiple myeloma and chronic leukemia.

The methods of the present invention allow specific inhibition of B cell maturation and antibody production without interfering with innate immunity or T cell mediated immunity. Current therapies block both T and B cell mediated immunity and are based on highly cytotoxic agents.

The newly discovered pathway required for maturation of B cells involves IκB kinaseα (IKKα), a protein which has been previously reported and the function initially reported to be an IκB kinase. However, the inventors have discovered that IKKα is not a "real" IκB kinase, and instead is an NF-κB2 kinase. The phosphorylation of NF-κB2 is required for B cell maturation.

This requirement for B cell maturation was demonstrated by generating a mouse strain in which IKKα is expressed at normal levels but cannot be activated; activation requires phosphorylation, but in the expressed IKKα the amino acids which are phosphorylated are replaced by an amino acids which are not a site of phosphorylation. These mice are healthy and exhibit normal innate immunity and T cell development. They only fail to mature their B cells and form secondary lymphoid organs.

Therefore, the present invention provides a method of treating and/or preventing pathologies of B cell or antibody origin, comprising inactivating IKKα by preventing its phosphorylation. In some embodiments, IKKα is inactivated by administering a compound which prevents its phosphorylation; such compounds are screened as described below. In other embodiments, IKkα is knocked out and replaced with a mutant IKKα in which amino acid serine at position 176, amino acid serine at position 180, or both amino acids are replaced by another amino acid; in some specific embodiments, the amino acids are replaced by alanine.

The present invention also provides means to screen compounds which prevent phosphorylation of IKKα, comprising providing a composition comprising IKKα, a phosphorylation source, a kinase which phosphorylates IKKα, and a compound to be screened, and detecting phosphorylated IKKα. In some embodiments, the compounds prevent phosphorylation of amino acid serine at position 176, amino acid serine at position 180, or both amino acids. In other embodiments, the compounds prevent phosphorylation specifically of IKKα.

The present invention also provides mice in which IKKα is expressed as an altered form which is not phosphorylated. In some embodiments, the alterations comprise replacing amino acids which are phorphorylated; in specific embodiments, serine amino acids at positions 176 and 180 are replaced by alanines.

The present invention also provides means to screen compounds which prevent B cell maturation, comprising providing a mouse and a compound to be tested, treated the mouse with the compound, and detecting the presence of B cell maturation. In some embodiments, a compound acts by preventing phosphorylation of IKKα; the activity of the compound is determined by detected phosphorylated IKKα.

I. Development of the Present Invention

B cell maturation involves gene activation regulated by transcription factors, including nuclear factor-κB.

Nuclear factor-κB (NF-κB) is a collective name for inducible dimeric transcription factors composed of members of the Rel family of DNA-binding proteins that recognize a common sequence motif. The NF-κB transcription factors are involved in the activation of an exceptionally large number of genes in response to inflammation, viral and bacterial infections, and other stressful situations requiring rapid reprogramming of gene expression. Although NF-κB functions in the nucleus, it is normally sequestered in an inactive form in the cytoplasm of nonsimulated cells; consequently, it must be translocated to the nucleus to function. The subcellular location of NF-κB is controlled by a family of inhibitory proteins, Inhibitor of κB (IκB), which bind to NF-κB and mask its nuclear localization signal, thereby preventing nuclear uptake. Exposure of cells to a variety of extracellular stimuli leads to the rapid phosphorylation, ubiquitinylation, and ultimately proteolytic degradation of IκB, which frees NF-κB to translocate to the nucleus and activate the transcription of its target genes.

The inducible phosphorylation of IκB is catalyzed by a multisubunit IκB kinase (IKK), which appears to be the initial point of convergence for most stimuli that activate NF-κB. IKK is itself rapidly activated by phosphorylation, and then phosphorylates IκB at two critical serines in the N-terminal regulatory domain. IKK contains two catalytic subunits, IKKα and IKKβ, and a regulatory subunit, IKKγ (also called NEMO). The two catalytic subunits have structural similarities, and both can phosphorylated IκB in vitro. However, they have distinct physiological functions, as evidenced by gene knock out experiments. The results indicated that of the two catalytic subunits, only IKKβ is essential for the activation of NF-κB in response to proinflammatory stimuli, where activation occurs by inducible IκB phosphorylation and degradation. The second catalytic subunit, IKKα, appears to play a critical role in developmental processes, in particular the formation and differentiation of epidermis, where it appears to be essential for keratinocyte differentiation.

However, the inventors have discovered a new function of IKKα, which is a preferential NF-κB2 kinase, and that this activity requires its activation by NIK (NF-κB inducing kinase). Thus, the inventors have determined that IKKα and NIK comprise a second NF-κB activation pathway responsible for B-cell maturation that is based on regulated NF-κB2 processing rather than IκB degradation. Therefore, IKKα is required for B-cell maturation, formation of secondary lymphoid organs, and processing of the NF B2/p100 precursor.

A. Maturation of B Cells

B-cell maturation and differentiation is an ordered process that results in the expression of immunoglobulins (Igs). Immunoglobulins (i.e., antibodies) are extremely important components of the immune system, due to their recognition of and binding to antigens, as well as their involvement in the initiation of various biologic processes that are independent of antibody specificity. Immunoglobulins comprise an extremely diverse family of proteins, although each is made up of two related polypeptides, namely light chains and heavy chains. The heavy chains are approximately twice as large as the light chains. Each Ig contains equal numbers of heavy and light chain polypeptides that are held together by non-covalent forces and covalent interchain disulfide bridges. The N-terminal domain of heavy and light chains is referred to as the "variable region," ($V_H$ and $V_L$, respectively). The other domains within these chains are collectively referred to as the "constant region" ($C_H$ and $C_L$, respectively). It is the variable region that gives antibodies their specificity for a particular antigen. The light chains can be classified into two distinct types, referred to as kappa (κ) and lambda (λ). In humans, five different subclasses of heavy chains are expressed. These subclasses differ significantly in their $C_H$ sequences. The five heavy chains are designated as δ, μ, γ, α, and ε; Igs that contain these heavy chains are referred to as IgD, IgM, IgG, IgA, and IgE, respectively. Immunoglobulins can either exist as membrane-bound or secreted entities. The membrane forms are anchored to the B-cell surface by a portion of the heavy chains.

In mammals, B-cells develop from hematopoietic stem cells present in the bone marrow. This development is accompanied by DNA rearrangements that assemble the immunoglobulin genes. The first rearrangement occurs in a population of mitotically active bone marrow cells that are sometimes referred to as "pro-B cells." These cells express the surface proteins CD 10 and CD 19, and are the most primitive recognizable cells in the B-cell lineage. In addition, these cells express the nuclear proteins terminal deoxynucleotidyl transferase (TdT) and recombination-activating gene products RAG-1 and RAG-2. The first rearrangement that occurs in pro-B cells is the joining of two segments ($D_H$ and $J_H$) in the heavy chain genes. This is followed by joining of the $V_H$ segment to the fused $D_H/J_H$ segment. Successful V/D/J rearrangement results in the synthesis of heavy chain proteins. The heavy chains produced at this stage in B cell development are of the μ type and contain a short hydrophobic region that allows them to integrate into cellular membranes. The membrane-associated form of μ protein is referred to as "$\mu_m$." Heavy chains usually cannot be transported to the cell surface unless they are complexed with light chains. Thus, pro-B cells express two proteins referred to as "surrogate light chains" that can bind to heavy chains, take the place of light chains, and be displayed transiently on membranes of pro-B cells.

After a series of events within the cells, pro-B cells progress to the next stage of development to produce "pre-B cells." Pre-B cells do not yet express immunoglobulin light chains, but contain ($\mu_m$) intracellularly. These cells are almost exclusively present in the bone marrow and represent a transient stage in B-cell development. Upon entering the pre-B cell stage, the B-cell precursors divide several times in response to interleukin 7 (IL-7) produced locally by stromal cells in the bone marrow. Pre-B cells then stop dividing and mitosis does not resume until the cells develop into fully mature B cells and encounter antigen in the periphery (i.e., away from the bone marrow).

After another series of events within the pre-B cells that result in the expression of membrane-bound IgM, the cells enter the B-lymphocyte stage of development. Indeed, once surface IgM is expressed, the cells are considered to be "B lymphocytes" (or "B cells"). However, these "immature B lymphocytes" are not yet ready to participate in the immune response. Thus, they remain in the bone marrow for an additional period before exiting to the periphery, where their maturation continues, primarily within the spleen. During this process, the cells acquire additional surface molecules that identify them as "mature B cells." Although individual B-cell lineages differ in the types and amounts of surface markers and/or the sequence in which they acquire these markers, the following discussion outlines a general developmental pathway.

In addition to IgM, mature B cells also express surface IgD. The IgM and IgD expressed by any individual B cell incorporate the same light chains and have identical antigen specificity. Other surface markers expressed by mature B cells include complement receptors (e.g., CR1 and CR2), a membrane-anchored enzyme referred to as "5'-nucleotidase" (CD73), CD23 (a lectin-like oligosaccharide-binding protein), leukocyte function associated antigen (LFA-1), intercellular adhesion molecule-1 (CAM-1), and CD22. Individual cells also express other markers, including surface-homing receptors that target them to particular sites within the body (e.g., lymph nodes). The cells also acquire major histocompatibility complex (MHC) proteins, which enable them to present antigens to T-cells (i.e., T-helper cells). In addition, the cells begin to express CD40, which is involved in receiving T-cell help. Initially, B cells express antibodies of low affinity and specificity. However, through the process of hypermutation, which occurs within germinal centers of the spleen, B cells undergo affinity maturation and become capable of expressing antibody molecules of high affinity and specificity. Germinal center formation is dependent upon the interactions between B and T cells, as well as stromal and dendritic cells within the spleen. Upon acquisition of these various markers, the mature B cells become competent for immune system function.

Upon activation, B-cells divide to produce cells that either become "memory" cells or "plasma" cells. Most B cells within a proliferating clone do not differentiate into plasma cells, but revert to a resting state as memory B cells. Many of these memory cells become resident within lymphoid follicles, where they can survive for years and be activated many years after their initial development. Upon subsequent activation, the memory cells undergo further replication cycles and produce additional memory and plasma cells. The majority of plasma cells reside in the bone marrow, where they become essentially "antibody factories" as they switch from producing membrane-bound antibody to secreting large amounts of antibodies. Thus, these cells are largely responsible for the production of circulating antibodies in response to an immunologic challenge.

B. Discovery of Role of IKKα in B Cell Maturation

Mammals express five NF-κB transcription factors, designated as RelA, RelB, c-Rel, NF-κB1, and NF-κB2 (Ghosh et al., Ann. Rev. Immunol., 16:225 [1998]). Unlike the Rel proteins, NF-κB1 and NF-κB2 are synthesized as large precursors, p105 and p100, which require proteolytic processing to produce the p50 and p52 NF-B subunits (Ghosh et al., supra). Mature NF-κB dimers are kept in the cytoplasm through interaction with inhibitory proteins (IκBS) and the major pathway leading to their activation is based on inducible IκB degradation (Ghosh et al., supra; and Rothwarf and Karin, supra). This major or canonical pathway is rapidly triggered by pro-inflammatory cytokines and components of bacterial and viral pathogens, requiring activation of the IκB kinase (IKK) complex (Rothwarf and Karin, supra; and Karin et al., Ann. Rev. Immunol., 18:621 [2000]). As the NF-κB1 and NF-κB2 precursors contain IκB-like ankyrin repeats in their C-termini, they are able to function as IκBs (Rice et al., Cell 78:773 [1992]; and Mercurio et al., Genes Develop., 7:705 [1993]). However, processing or degradation of p105 and p100 are not induced by the same stimuli that cause rapid IκB degradation (Karin et al., Ann. Rev. Immunol., 18:621 [2000]). Processing of NF-κB1 is largely a constitutive process (Karin et al., Ann. Rev. Immunol., 18:621 [2000]; and Lin et al., Cell 92:819 [1998]). Although NF-κB1 degradation can be induced by overexpression of the MAP kinase kinase kinase (MAPKKK) Cot/TPL-2, Cot$^{-/-}$ mice do not exhibit defective NF-κB activation (Dumitru et al., Cell 103:1071 [2000]). However, it is contemplated that NF-κB2 processing is a regulated process, as it is most pronounced in mature B cell lines (Liou et al., Mol. Cell. Biol., 14:5349 [1994]) and is defective in alymphoplasia (aly) mice (Yamada et al., J. Immunol., 165:804 [2000]). The aly mutation, which maps to the gene coding for NF-κB inducing kinase (NIK), another MAPKKK, interferes with development of primary and secondary lymphoid organs (Shinkura et al., Nat. Genet., 22:74 [1999]), as does a complete NIK-deficiency (Yin et al., Science 291:2162 [2001]). Interestingly, NIK induces ubiquitin-dependent processing of NF-κB2 through phosphorylation of its C-terminus (Xiao et al., Mol. Cell., 7:401 [2001]), but has no effect on total NF-κB DNA binding activity (Yin et al., supra).

NIK was first found as an NF-κB activating kinase (Malinin et al., Nature 385:540 [1997]) and was later shown to phosphorylate and activate IKKα (Ling et al., Proc. Natl. Acad. Sci. USA 95:2791 [1998]) (i.e., one of the two catalytic subunits of the IKK complex [Rothwarf and Karin, supra]). The other catalytic subunit, IKKβ, is 52% identical to IKKα, and in vitro, both subunits exhibit IκB kinase activity (Zandi et al., Cell 91:243 [1997]; Zandi et al., Science 281:1360 [1998]; Mercurio et al., Science 278:860 [1997]; and Woronicz et al., Science 278:866 [1997]). Despite these similarities, IKKα and IKKβ have distinct physiological and regulatory functions (Rothwarf and Karin, supra; and Karin et al., Ann. Rev. Immunol., 18:621 [2000]). Whereas IKKβ is essential for proper activation of NF-κB in response to pro-inflammatory stimuli and prevention of TNF-α induced apoptosis (Li et al., Science 284:321 [1999]; Li et al., J. Exp. Med., 189:1839 [1999]; Tanaka et al., Immun., 10:421 [1999]; Chu et al., Immun., 11:721 [1999]; and Senftleben et al., Immun., 14:217 [2001]), IKKα is dispensable for IKK and NF-κB activation by pro-inflammatory stimuli (Chu et al., supra; and Hu et al., Science 284:316 [1999]). IKKα, but not IKKβ, is essential for proper skeletal morphogenesis and differentiation of the epidermis (Hu et al., supra; and Takeda et al., Science 284:313 [1999]). However, this function of IKKα does not depend on its IKK activity or NF-κB activation (Hu et al., Nature 410:710 [2001]). Thus, one question addressed during the development of the present invention is whether IKKα has any NF-κB-related functions that are masked by the perinatal lethality of Ikkα$^{-/-}$ (e.g., in mice).

During the development of the present invention, radiation chimeras whose hematopoietic system is derived from Ikkα$^{-/-}$ stem cells and knock-in mice that lack the activating phosphorylation sites of IKKα were developed. Using these chimeras and knock-ins, it was determined that IKKα kinase activity is required for B cell maturation and formation of secondary lymphoid organs. Importantly, it was determined that IKKα is required for NIK-induced NF-κB2 processing. Thus, rather than playing an essential role in the NF-κB signaling pathway based on IκB degradation, IKKα is required for a second NF-κB activation pathway based on NF-κB2 processing. This pathway is strikingly related to the IKK-dependent NF-κB activation pathway of Drosophila, which is based on proteolytic processing of Relish, a NF-κB-like precursor protein (Silverman et al., Genes Develop., 15:104 [2001]; and Lu et al., Genes Develop., 15:104 [2001]). In addition to elucidating the function of IKKα, the results obtained during the development of the present invention shed new light on the evolution of innate and adaptive immunity.

1. Differential Requirement for IKKα and IKKβ in Lymphoid Development

Analysis of bone marrow cells from wild-type (wt), Ikkα$^{-/-}$ and Ikkβ$^{-/-}$ radiation chimeras (See, Example 3, below) revealed the complete absence of B-cells in the Ikkβ$^{-/-}$ derived samples, as shown in FIG. 1, Panel A. This was confirmed by the absence of immunoglobulin heavy chain gene rearrangement in the bone marrow cells of these animals. In contrast, B cells were present in Ikkα$^{-/-}$ bone marrow (See, FIG. 1, Panel A). Although these cells expressed normal levels of early B cell markers, a B220$^{hi}$CD24$^{lo}$ population, representing circulating mature B cells, was absent. Ikkβ$^{-/-}$ reconstituted spleen and lymph nodes lacked lymphoid cells and exhibited very abnormal architecture, while Ikkα$^{-/-}$ reconstituted spleen and lymph nodes appeared to be grossly normal. However, flow cytometric analysis revealed low frequency of B220$^+$ cells in the latter, as shown in FIG. 1, Panel B. No differences in thymocytes and peripheral T-cell populations were found between wt and Ikkα$^{-/-}$ radiation chimeras. This is in marked contrast to the Ikkβ$^{-/-}$ radiation chimeras, which completely lack B and T cells (Senftleben et al., supra). Analysis of typical B cell markers in Ikkα$^{-/-}$ spleen and lymph nodes revealed a pronounced reduction of the mature IgM$^{lo}$IgD$^{hi}$ population compared to virgin IgM$^{hi}$ B cells (See, FIG. 1, Panel B). Whereas the splenic B to T-cell ratio was almost normal six weeks after reconstitution with Ikkα$^{-/-}$ stem cells, it was significantly reduced thereafter (See, FIG. 1, Panel C). The loss of mature IgM$^{lo}$IgD$^{hi}$ cells makes the largest contribution to the paucity of B cells in Ikkα$^{-/-}$ radiation chimeras (FIG. 1, Panel D). This defect in B lymphopoiesis is cell-autonomous and is not suppressed by co-transplantation of wt bone marrow (data not shown).

2. Decreased Lifespan of Peripheral Ikkα$^{-/-}$ B Cells

Figure 2:
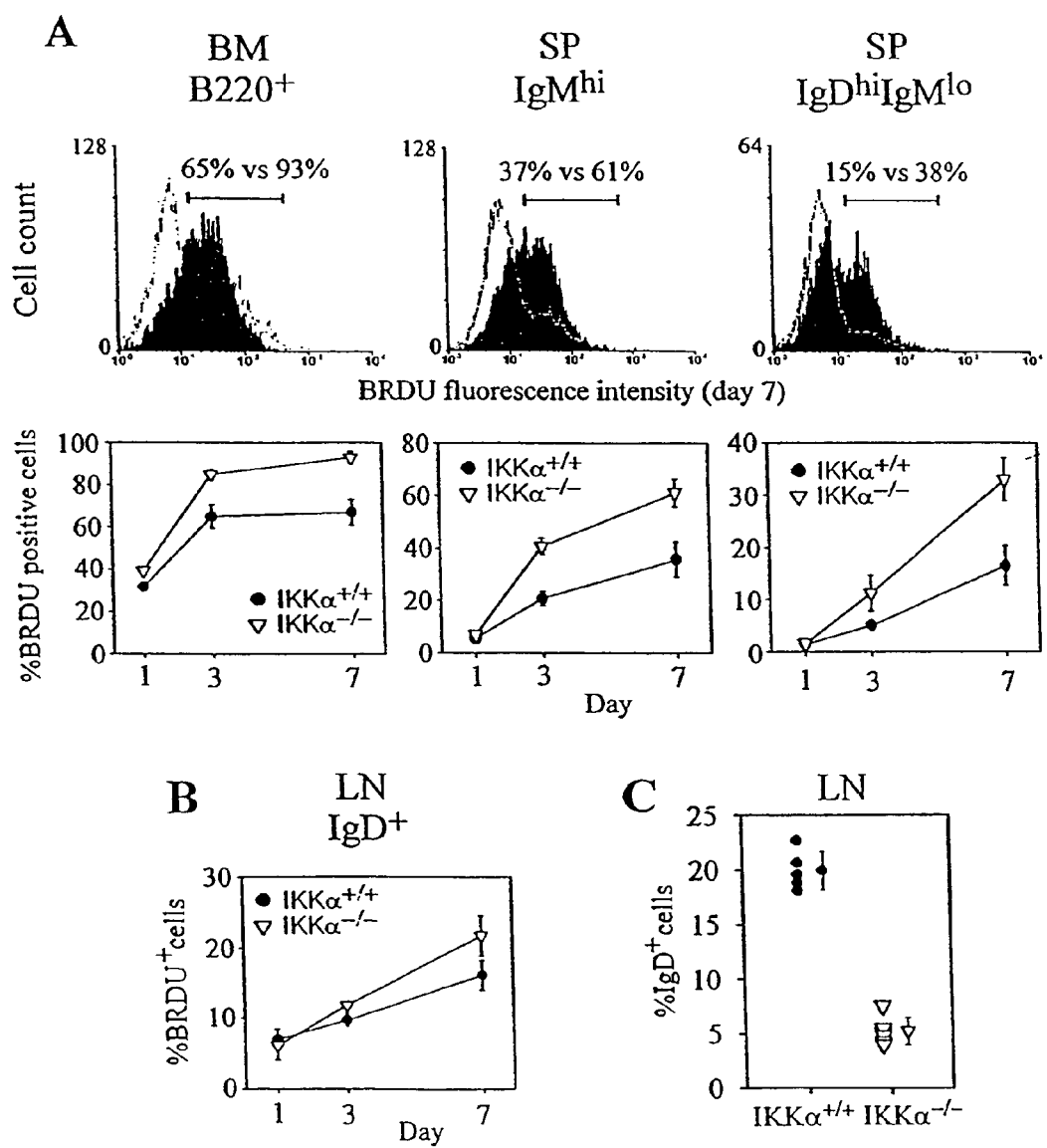
FIG. 2 provides data showing the increased turnover of ±Ikkα$^{-/-}$ B cells in BrdU incorporation experiments. The turnover of virgin (IgM$^{hi}$) and mature (IgM$^{lo}$IgD$^{hi}$) B-cells was determined by means of BrdU incorporation. Eight weeks post-engraftment, mice were administered BrdU. Bone marrow (BM), splenocytes (SP), and lymph node (LN) cells were analyzed by flow cytometry after three-color staining for BrdU, IgM and IgD. The regions used for gating of virgin and mature B cells are as shown in FIG. 1, Panel B. The top row of Panel A shows BrdU incorporation into bone marrow B220$^+$ cells, virgin (IgM$^{hi}$) and mature (IgM$^{hi}$IgD$^{lo}$) splenic B-cells of Ikkα$^{+/+}$ (grey plots) and Ikkα$^{-/-}$ (black plots) radiation chimeras, determined after 7 days of labeling. The bottom row of Panel A provides the kinetics of BrdU incorporation into the same cell types shown in the top row over a 7 day period. Values represent means±SD for 3 mice in each group and time point. Panel B provides results of BrdU incorporation experiments using IgD$^+$ lymph node cells (n=3 each group, mean±SD) for Ikkα$^{+/+}$ (wt) and Ikkα$^{-/-}$ cells. Panel C provides the frequencies of mature IgD$^+$ lymph node B-cells in Ikkα$^{+/+}$ and Ikkα$^{-/-}$ radiation chimeras (n=5 each group, mean±SD).

To assess whether the paucity of peripheral Ikkα$^{-/-}$ B cells is due to reduced production or decreased survival, B cell turnover was determined using bromodeoxyuridine (BrdU) labeling, as described in Example 1. Ikkα$^{-/-}$ B-cells incorporated between one-third (bone marrow) and two-fold (spleen) more BrdU than wt B cells, as shown in FIG. 2, Panel A. This difference tended to be more pronounced in mature (i.e., IgM$^{lo}$IgD$^{hi}$), rather than virgin (IgM$^{hi}$) B-cells (See, FIG. 2, Panel A). Given the fact that only few IgD$^+$ cells were detectable in Ikkα$^{-/-}$ reconstituted lymph nodes, the smaller difference in the number of BrdU$^+$IgD$^+$ wt and Ikkα$^{-/-}$ cells was somewhat surprising (See, FIG. 2, Panel B). Although an understanding of the mechanism(s) is not necessary in order to use the present invention and it is not intended that the present invention be limited to any particular mechanism, it is contemplated that this result may be caused by high B cell turnover in the spleen, leading to a lower fraction of circulating mature B-cells (See, FIG. 2, Panel B). Consequently, the frequency of mature IgD$^+$ B-cells was found to be significantly lower in Ikkα$^{-/-}$ lymph nodes, as indicated in FIG. 2, Panel C. However, it is contemplated that these results are most likely caused by a block in B cell maturation.

Figure 3:
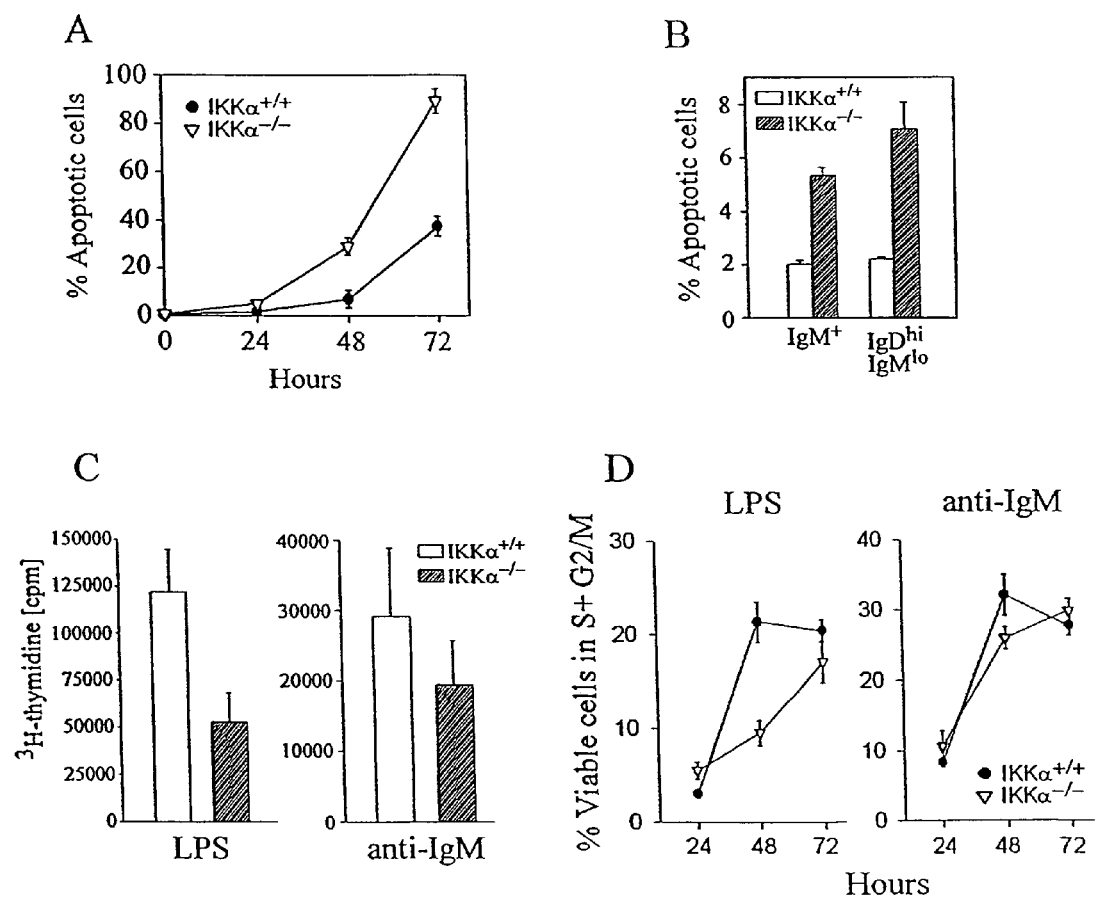
FIG. 3 provides data showing that Ikkα$^{-/-}$-deficient B-cells exhibit higher apoptotic rates and diminished mitogenic responses, particularly as compared to wild-type (Ikkα$^{+/+}$) cells. Panel A shows spontaneous apoptosis in vitro for CD43$^-$ resting splenic B-cells purified and cultured without stimulation for 72 hours. At 24 hour intervals the percentages of apoptotic cells were determined by 7-AAD staining. Initially, more than 97% of the cells were viable (n=3 each group, mean±SD). Panel B shows the relative rates of spontaneous apoptosis in virgin and mature splenic B cells. After 24 hours without stimulation, purified resting B-cells were stained for IgM and IgD, and apoptotic cells were detected by annexin-V staining (n=3 each group, mean±n SD). Purified resting B-cells (>97% viable) were stimulated with LPS and anti-IgM for 24 hours, and proliferation was determined by $^3$H-thymidine incorporation for 16 hours as shown in Panel C. Panel D provides results for purified resting splenic B-cells (>98% in G$_0$/G$_1$) stimulated by LPS or IgM and analyzed by flow cytometry after staining with propidium iodide. The results show relative amounts of viable B-cells in S+G$_2$/M. The data represent means±SD of 3 independent experiments.

The increased turnover of Ikkα$^{-/-}$ B-cells correlates with higher rates of spontaneous apoptosis (See, FIG. 3, Panel A). Staining of early apoptotic cells with either IgM or IgD revealed a more pronounced increase in the apoptotic rate of mature IgD$^{hi}$ B cells (See, FIG. 3, Panel B). Increased apoptosis was also observed in vivo, as described below. Ikkα$^{-/-}$ B-cells were also found to exhibit defects in mitogenic responses. After stimulation with lipopolysaccharide (LPS), Ikkα$^{-/-}$ cells were found to incorporate half as much $^3$H-thymidine as wt cells and exhibited a more modest reduction in the response to anti-IgM (See, FIG. 3, Panel C). However, cell cycle analysis of purified B cells suggested that the impaired proliferation of Ikkα$^{-/-}$ cells is mostly due to their higher apoptotic rates, as the cell cycle progression rates of viable wt and Ikkα$^{-/-}$ cells were similar (See, FIG. 3, Panel D).

3. Defective Germinal Center Formation and Increased Splenic Apoptosis

Figure 4:
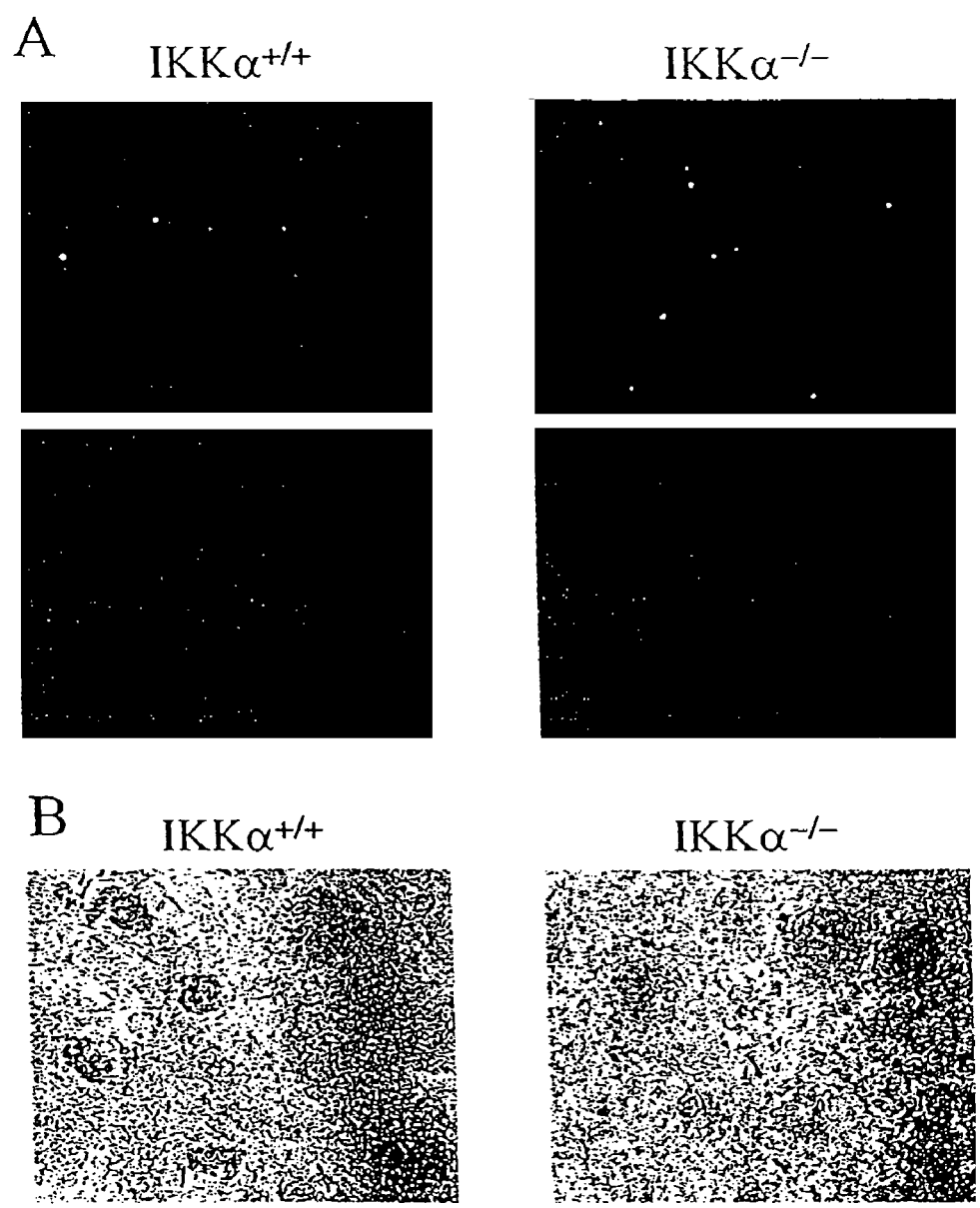
FIG. 4 provides data showing impaired germinal center formation and increased splenic apoptosis in Ikkα$^{-/-}$ radiation chimeras. Panel A shows results for spleens removed from wt (Ikkα$^{+/+}$) and Ikkα$^{-/-}$ radiation chimeras analyzed by TUNEL staining for the presence of apoptotic cells. The lower row shows DAPI staining results for the same areas. Panel B provides data for wt (Ikkα$^{+/+}$) and Ikkα$^{-/-}$ radiation chimeras injected with TNP-KLH. After 12 days, the spleens were stained with PNA and counterstained with hematoxylin. As indicated, almost no GC formation is detectable in Ikkα$^{-/-}$ reconstituted spleens.

To determine whether the B cell immune responses dependent upon interactions with T cells were functional, mice were immunized with dinitrophenol-keyhole limpet hemocyanin (DNP-KLH) adsorbed to alum, as described in Example 2. The formation of germinal centers (GC) in the animals was evaluated 12 days after immunization (See, Example 2). Wt spleens exhibited numerous GCs characterized by B cell areas that bound peanut hemagglutinin (PNA). In contrast, the spleens of Ikkα$^{-/-}$ radiation chimeras contained very few PNA-stainable cells (See, FIG. 4, Panel B). TUNEL staining (Senftleben et al., Immun., 14:217 [2001]) revealed higher numbers of apoptotic cells in spleens of non-immunized Ikkα$^{-/-}$ radiation chimeras (See, FIG. 4, Panel A).

Figure 5:
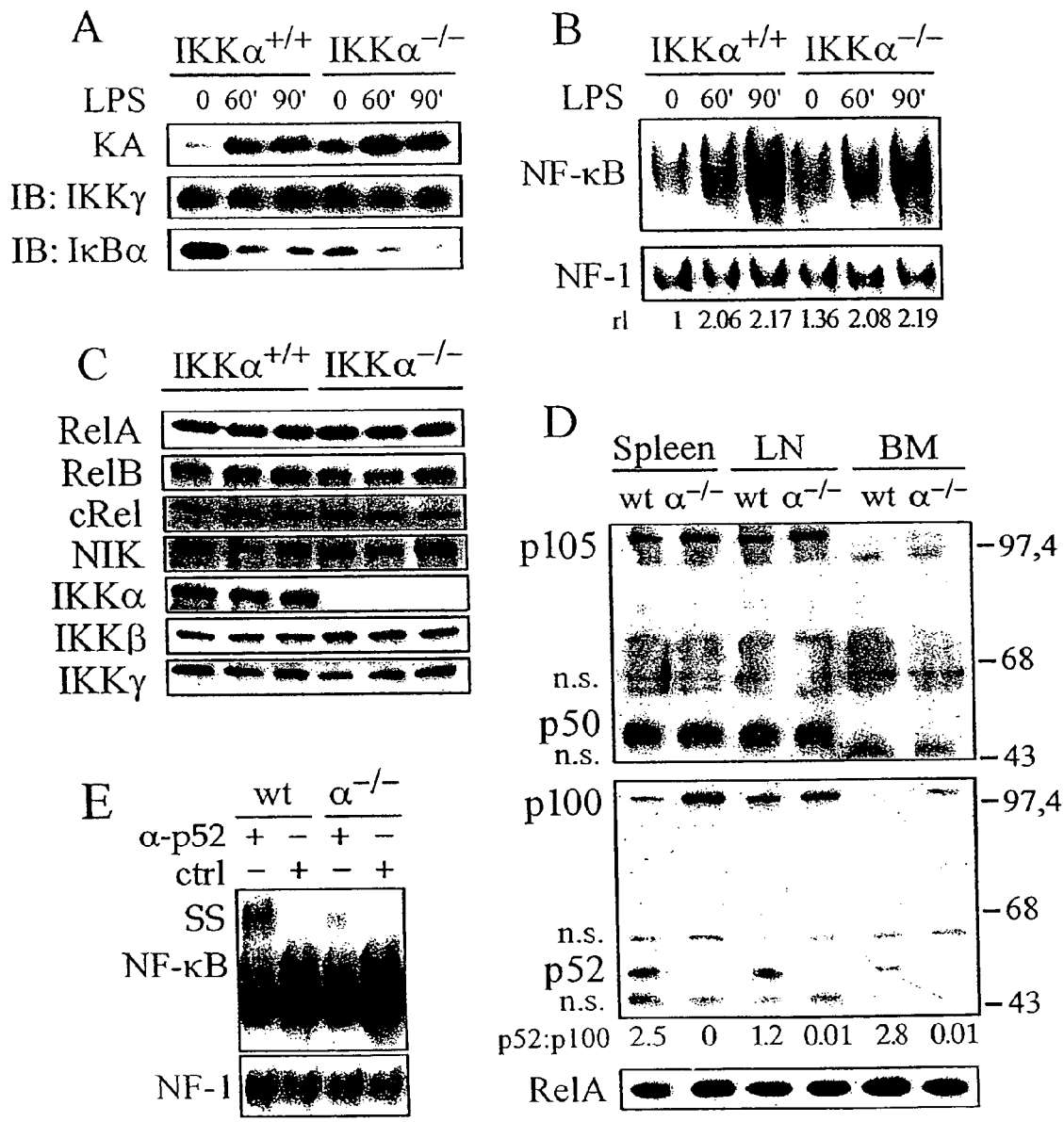
FIG. 5 provides results showing normal NF-κB DNA binding, but defective NF-κB2 processing in Ikkα$^{-/-}$ radiation chimeras. Panel A provides results for purified splenic B cells stimulated with 5 μg/ml LPS. IKK activity and Iκ Bα levels were determined at the indicated time points. IKK recovery was determined by immunoblotting (IB) with anti-IKKγ antibody. Panel B provides results for NF-κB and NF-1 DNA-binding activities in purified splenic B cells treated with 5 μg/ml LPS determined at the indicated time points. Panels A and B are representative of at least 5 independent experiments and the average relative levels (rl) of NF-B DNA binding activity in these experiments are indicated below. Panel C shows the expression levels of the indicated NF-κB proteins, NIK and IKK subunits examined by immunoblotting. Three individual wild-type and Ikkα$^{-/-}$ radiation chimeras were analyzed. Panel D provides results for splenic, lymph node (LN), and bone marrow (BM) B cells from groups of 3 wild-type and 3 Ikkα$^{-/-}$ radiation chimeras pooled and analyzed by immunoblotting for expression of NF-B1 (p105 and p50), NF-κB2 (p100 and p52) and RelA polypeptides. Panel E provides results for splenic B cells analyzed for their content of p52-containing NF-κB complexes. Nuclear extracts from B cells pooled from 3 different wild-type and Ikkα$^{-/-}$ radiation chimeras were incubated with a palindromic NF-κB binding site in the presence of either anti-p52 (Upstate Biotechnology, #06-413), or a control antiserum that does not recognize p52. Extract quality was monitored by binding to an NF-1 probe. In this Panel, "SS" refers to super-shifted p52-containing complexes.

4. Normal NF-κB DNA Binding, but Defective NF-κB2 Processing in Ikkβ$^{-/-}$ B Cells The absence of IKKα can be compensated for by IKKβ in liver and keratinocytes, leading to normal IKK and κNF-B activation by pro-inflammatory stimuli (Hu et al., Science 284:316 [1999]; and Hu et al., Nature, supra). Biochemical analysis of purified resting and stimulated B cells from radiation chimeras yielded similar results. Basal IKK activity was elevated in Ikkα$^{-/-}$ B-cells, as shown in FIG. 5, Panel A. This was associated with decreased Iκ Bα levels (See, FIG. 5, Panel A), and somewhat higher basal NF-κB DNA binding activity, as shown in FIG. 5, Panel B. However, LPS-induced IKK (See, FIG. 5, Panel A) and NF-κB DNA binding (See, FIG. 5, Panel B) activities were similar in Ikkα$^{-/-}$ and wt B-cells. These results were highly reproducible and observed upon analysis of at least five individual pairs of radiation chimeras. The expression of individual NF-κB proteins between wt and Ikkα$^{-/-}$ B-cells were compared. Similar levels of RelA, c-Rel, RelB, NF-κB1 p105 and p50 were observed (See, FIG. 5, Panel C). However, Ikkα$^{-/-}$ B-cells exhibited defective processing of NF-κB2 and contained much less p52, but more p100 than wild-type cells (See, FIG. 5, Panel D). This defect was present in bone marrow, spleen, and lymph node-derived B cells and was independent of the level of NF-κB2 expression (See, FIG. 5).

5. NF-κB2 Processing and B Maturation Require IKKα Phosphorylation

Figure 6:
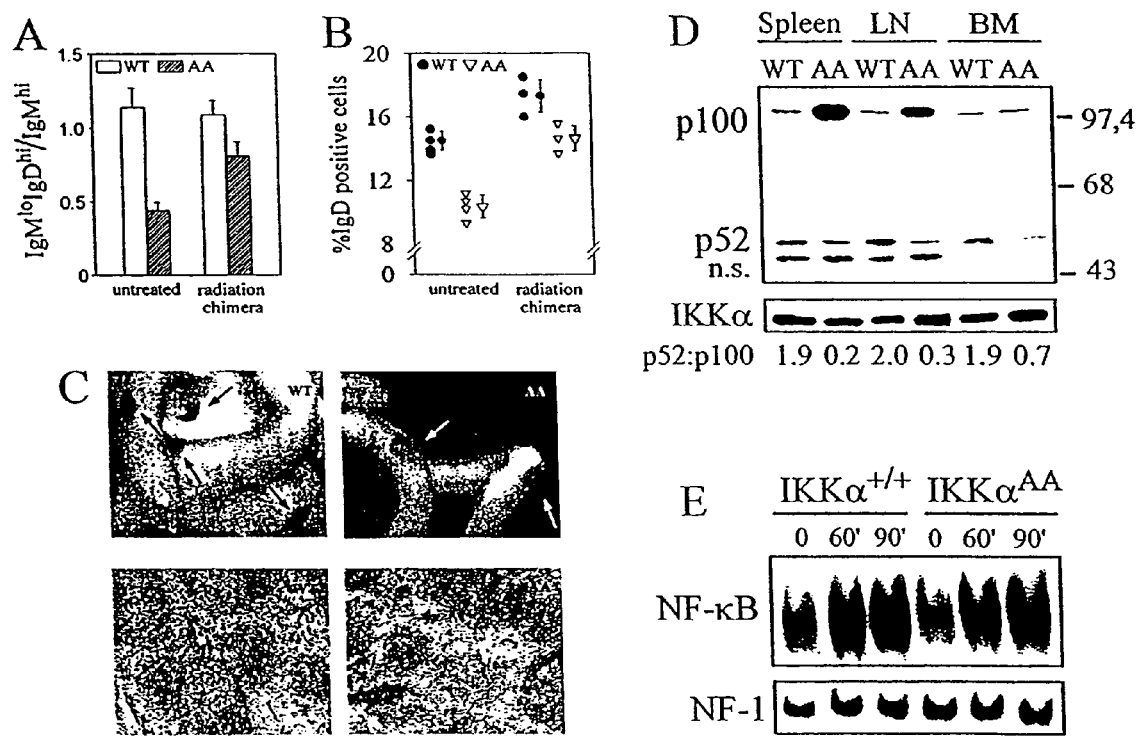
FIG. 6 provides data showing that IKKα phosphorylation is required for B-cell maturation and NF-κB2 processing. Panel A provides the ratio of virgin (IgM$^{hi}$) to mature (IgM-$^{lo}$IgD$^{hi}$) splenic B cells in untreated wt and Ikkα$^{AA}$ mice and radiation chimeras as determined by flow cytometry. The bar graphs show means±SEM for 3 animals in each group. Panel B provides the relative frequencies of mature IgD$^+$ lymph node B-cells in untreated wt and Ikkα$^{AA}$ mice. To examine GC formation, mice were immunized with DNP-KLH and examined 12 days later. Peyer's patches were visualized by staining with anti-VCAM1 antibody as shown in Panel C. Panel D provides immunoblot analysis data showing NF-κB2 processing in purified B cells from spleen, lymph nodes (LN) and bone marrow (BM) of untreated wt and Ikkα$^{AA}$ mice. Data are representative of 3 independent experiments. Panel E shows NF-1 DNA binding activities assessed by immunoblots for splenic cells from wt (Ikkα$^{+/+}$) and Ikkα$^{AA}$ mice stimulated with LPS and NF-B.

To determine the role of IKKα phosphorylation by upstream kinases such as NIK, which is also required for B-cell maturation and GC formation (Yamada et al., J. Immunol., 165:804 [2000]), Ikkα$^{AA}$ knock-in mice were generated. In these animals, the activating phosphorylation sites of IKKα, serines 176 and 180, were replaced by alanines (See, Example 4). Although these Ikkα$^{AA}$ mice are viable, experiments were conducted to analyze the effect of this mutation on B-cell development under the same conditions as the Ikkα$^{-/-}$ null mutation. Thus, Ikkα$^{AA}$ radiation chimeras were generated. A reduction in mature IgD$^+$ B-cells was observed in the spleen and lymph nodes of these animals, as compared to wt radiation chimeras, as shown in FIG. 6, Panels A and B. However, a more pronounced deficiency of mature B cells was detected in untreated Ikkα$^{AA}$ mice that were 12 weeks of age (See, FIG. 6, Panels A and B). In addition, untreated Ikkα$^{AA}$ mice lacked distinct Peyer's patches and exhibited defective GC formation after immunization with DNP-KLH (See, FIG. 6, Panel C). Less severe defects were found in Ikkα$^{AA}$ radiation chimeras. Untreated Ikkα$^{AA}$ mice also exhibited defective NF-κB2 processing in purified B-cells of spleen and lymph nodes, as well as in bone marrow cells, which express lower levels of NF-κB2, as shown in FIG. 6, Panel D. The reduction in NF-κB2 processing (approximately 80%) was a bit lower than that caused by the complete IKKα deficiency. In contrast, both basal and LPS-induced NF-κB DNA binding activities in Ikkα$^{AA}$ B-cells were similar to those in wt cells, as shown in FIG. 6, Panel E. The defect in induction of certain NF-κB target genes, as shown in the Table in FIG. 7.

6. IKKα Acts Downstream to NIK

The results described above indicate that IKKα needs to be phosphorylated at its activation loop to support NF-κB2 processing in B-cells. In addition to autophosphorylation of IKK, these sites can be phosphorylated by NIK (Ling et al., supra). Like IKKα, NIK is required for NF-κB2 processing (Yamada et al., supra; and Xiao et al., supra). Although NIK overexpression was shown to stimulate NF-κB2 phosphorylation (Xiao et al., supra), the results described above suggested that NIK acts via IKKα. However, an understanding of the mechanism(s) is not necessary in order to use the present invention and it is not intended that the present invention be limited to any particular mechanism(s). Nonetheless, this was examined by co-transfection of NIK and NF-κB2 expression vectors into wt, Ikkα$^{-/-}$, and Ikkβ$^{-/-}$ mouse fibroblasts. Whereas NIK induced NF-κB2 processing in wt and Ikkβ$^{-/-}$ cells, it did not do so in Ikkα$^{-/-}$ cells, as shown in FIG. 7, Panel A. However, re-expression of IKK in Ikkα$^{-/-}$ cells restored NIK's ability to induce NF-κB2 processing.

Figure 8:
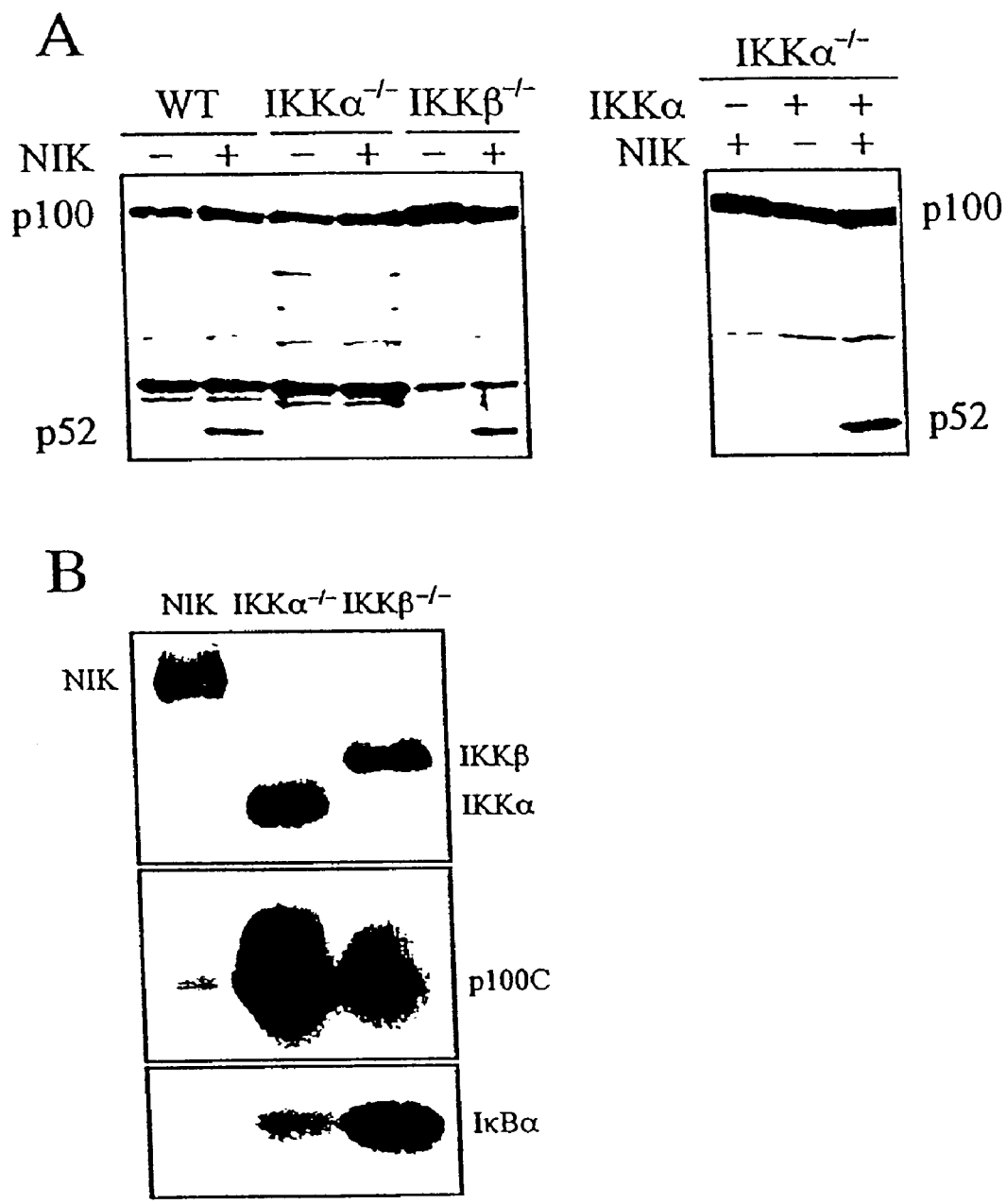
FIG. 8 provides data indicating that IKKα is required for NIK-induced NF-κB2 processing and is a potent NF-κB2 kinase. Panel A shows results from mouse fibroblasts derived from wt, Ikkα$^{-/-}$, and Ikkβ$^{-/-}$ embryos transfected with an NF-B2 p100 expression vector with or without NIK and IKKα expression vector. After 36 hours, the processing of NF-κB2 was examined by immunoblotting using an N-terminal specific p100 antibody. Panel B provides results for chromatographically pure IKKα and IKKβ (50 ng each) and immunopurified NIK, all produced in Sf9 cells using baculoviruses. These cells were examined for phosphorylation of GST-Iα Bβ (1-54) and GST-NF-κB (754-900) (p100C), as well as for autophosphorylation.

The abilities of recombinant NIK, IKKα and IKKβ (Zandi et al., Science 281:1360 [1997]) to phosphorylate the regulatory domains of Iκ Bα and NF-κB2 were also compared. As expected (Ling et al., supra), the regulatory domain of Iκ Bα was phosphorylated more efficiently by IKKβ than by IKKα, and not at all by NIK (See, FIG. 8, Panel B). However, the C terminal regulatory domain of NF-κB2 was phosphorylated most efficiently by IKKα. Despite its strong Iκ Bα kinase activity, IKKα was found to be a weak NF-κB2 C terminal kinase. Notably, this is the first demonstration of a clear difference in substrate specificities between IKKα and IKKβ that perfectly correlates with their different biological functions.

7. Summary

Although the mammalian IKK complex contains two catalytic subunits that share structural similarities, these subunits have distinct physiological functions (Rothwarf and Karin, supra). Also, although IKKβ's involvement in inducible Iκ Bα degradation and activation of NF-κB in response to infections and pro-inflammatory stimuli is unequivocally established (Li et al., Science, supra; Li et al., J. Exp. Med., supra; Tanaka et al., supra; Chu et al., supra; and Senftleben et al., supra), the role of IKKα in this process remained enigmatic until the development of the present invention. In the absence of IKKα, IKK complexes composed of IKKα dimers associated with IKKγ/NEMO do not provide sufficient Iκ Bα kinase activity (Li et al., J. Exp. Med., supra; Tanaka et al., supra; Chu et al., supra; and Senftleben et al., supra). Although it is not essential for the canonical NF-κB activation pathway, IKKα is required for proper patterning of the epidermis (Hu et al., Nature, supra; and Takeda et al., supra). However, this function is not mediated via IκBα or NF-κB, and does not require IKKα kinase activity (Hu et al., Nature, supra). These findings underscore the mystery that existed prior to the development of the present invention regarding the exact function of IKKα and its involvement in NF-κB activation. As described herein, IKKα is physiologically involved in NF-κB regulation, but instead of inducible Iκ Bα degradation, it exerts it NF-κB-relevant functions by regulating the processing of NF-κB2. However, an understanding of the mechanism(s) is not necessary in order to use the present invention and it is not intended that the present invention be limited to any particular mechanism(s).

Nonetheless, the results obtained during the development of the present invention indicate that the biochemical defect in NF-κB2 processing in Ikkα$^{-/-}$ or Ikkα$^{AA}$ B-cells is likely to account for their defective maturation and inefficient participation in formation of secondary lymphoid organs (e.g., Peyer's patches and GCs). Ikkα$^{-/-}$ splenic B cells showed deficient proliferative responses and enhanced spontaneous apoptosis, which may be the primary cause for the paucity of mature IKKα-deficient B-cells. In contrast, formation of immature IgM$^{hi}$ B-cells and T-cell development are not affected by the absence or inactivity of IKKα. Another group (Kashio et al., J. Exp. Med., 193:417 [2001]) recently reported similar defects. In their experiments, Kashio et al. reconstituted Rag2$^{-/-}$ mice with Ikkα$^{-/-}$ stem cells. These authors reported a modest, but general decrease in both basal and inducible NF-κB DNA binding activity in Ikkα$^{-/-}$ splenic B-cells. However, these results were not normalized and may have been influenced by the different composition of the B-cell population in the mutant.

Indeed, after multiple experiments and normalization to NF-1 binding activity conducted during the development of the present invention, it was not possible to detect a significant reduction in NF-κB DNA binding activity in Ikkα$^{-/-}$ or Ikkα$^{AA}$ B-cells. In contrast, Ikkα$^{-/-}$ B-cells exhibited a modest elevation in basal NF-κB binding activity, paralleling their higher basal IKK activity. Elevated basal IKK and NF-κB activities were also observed in Ikkα$^{-/-}$ keratinocytes and are probably due to the replacement of IKKα:IKKβ heterodimers with more active IKKβ:IKKβ homodimers (See, Hu et al., [2001] supra). Furthermore, the highly specific defect in B-cell maturation and absolutely normal T-cell development in Ikkα$^{-/-}$ radiation chimeras are inconsistent with a general NF-κB deficiency, which based on analysis of Ikkβ$^{-/-}$ radiation chimeras, adversely affects both B- and T-cells (Senftleben et al., supra). Similarly, the absence of NIK, which acts upstream of IKKα, does not affect total NF-κB DNA binding activity (Yin et al., supra). However, the inactivation of either NIK or IKKα causes a marked inhibition of NF-B2 processing. NF-κB1 processing, which appears to be a constitutive process (Lin et al., supra) is not affected.

Interestingly, expression of NF-κB2 is elevated in more mature B-cell lines (Liou et al., supra), and is upregulated during B-cell development (See, FIG. 6). Thus, the defect in B-cell maturation caused by the absence of IKKα correlates with this expression pattern. In addition, the complete knockout of the Nfkb2 gene results in similar, although not identical, defects to those caused by the Ikkα$^{-/-}$ or Ikkα$^{AA}$ mutations, including the absence of GCs (Caamano et al., J. Exp. Med., 187:185 [1998]; and Franzoso et al., J. Exp. Med., 187:147 [1998]). However, the Nfkb2$^{-/-}$ mutation was found to abolish expression of both p100 and p52, whereas the two Ikk mutations reduce p52 and increase p100 expression. It is contemplated that these differences account for some of the distinctions between the mutant phenotypes. However, an understanding of the mechanism(s) is not necessary in order to use the present invention and it is not intended that the present invention be limited to any particular mechanism(s).

The aly mutation, which interferes with NIK activation (Shinkura et al., supra), also results in defective NF-κB2 processing (Yamada et al., supra; and Xiao et al., supra) Furthermore, NIK over-expression stimulates NF-κB2 phosphorylation and processing (Xiao et al., supra). The results discussed herein strongly indicate that NIK acts via IKKα. First, the Ikkα$^{AA}$ mutation, which replaces the NIK phosphorylation sites of IKKα with alanines, inhibits NF-κB2 processing and B-cell maturation, as well as GC and Peyer's patch formation. Second, NIK fails to stimulate NF-κB2 processing in the absence of IKK. Third, IKK is a more effective NF-B2 C-terminal kinase than NIK. As both NIK and IKKα phosphorylate the C-terminal regulatory domain of NF-κB2, it is contemplated that they have overlapping substrate specificities in vitro. However, an understanding of the mechanism (s) is not necessary in order to use the present invention and it is not intended that the present invention be limited to any particular mechanism(s). Nonetheless, this is not surprising in view of the fact that the phosphorylation sites in NF-κB2 were first identified based on their sequence similarity to the activating phosphorylation sites of IKKα (Xiao et al., supra), which can be phosphorylated by both NIK and IKK itself (Ling et al., supra). However, the stronger NF-κB2 C-terminal kinase activity of IKKα indicates that the NIK immunoprecipitates used as an earlier source for NIK (Xiao et al., supra) may have contained IKKα. As indicated herein, based on the results obtained during the development of the present invention, it is now clear that NIK and IKKα are components of a specialized NF-κB activation cascade that targets NF-κB2, instead of Iκ Bαs. NIK itself is believed to be activated by the lymphotoxin (LT)β receptor (LT R), a member of the TNF receptor family (Shinkura et al., supra; and Yin et al., supra). Indeed, Ltβ r$^{-/-}$ mice exhibit defects similar to those of aly mice, which although broader, encompass those caused by the Ikkα$^{AA}$ mutation (Futterer et al., Immun., 9:59 [1998]). However, LT R is expressed in the stroma, but not in lymphoid cells and therefore cannot activate the NIK-IKKα-NF-κB2 pathway in the latter. A plausible activator of this pathway in B-cells is another member of the TNF receptor family, BLys, which is also required for B-cell maturation and GC formation (Yan et al., Nat. Immun., 1:37 [2000]). The adoptive transfer experiments described in Example 4 and illustrated in FIG. 6 indicate that IKKα phosphorylation, like NIK (Yamada et al., supra) expression or NF-κB expression, is required outside the B-cell compartment for proper maturation of the latter and formation of secondary lymphoid organs.

Thus, the present invention provides a novel function for IKKα that depends upon its protein kinase activity and can not be compensated for by the related IKKβ subunit. Thus, whereas both IKK catalytic subunits are involved in activation of NF-κB transcription factors, they do so via different mechanisms and substrates. While IKKβ is the canonical activator of NF-κB in response to infection, acting via the phosphorylation of Iκ Bs, IKKα is responsible for activation of a specific NF-κB factor required for B-cell maturation and formation of secondary lymphoid organs. This function is exerted through phosphorylation of NF-κB2 and is remarkably similar to the function of the *Drosophila* IKK complex, which contains a single catalytic subunit that is similar to both IKKα and IKKβ (Silverman et al., supra; and Lu et al., supra). Remarkably, DmIKK/Ird5 does not phosphorylate the single Iκ B of *Drosophila*, Cactus, and instead leads to activation of anti-bacterial genes through the phosphorylation-induced processing of the *Drosophila* NF-B1/2 homolog, Relish (Silverman et al., supra; and Lu et al., supra). However, while in *Drosophila* the processing-dependent NF-κB pathway is the major provider of innate antibacterial immunity (Lu et al., supra), in mammals, this pathway has been assigned to control a specific aspect of adaptive immunity, namely B-cell maturation and formation of secondary lymphoid organs. Thus, the duplication of IKK catalytic subunits and the divergence of their functions correlates with the appearance of adaptive immunity.

II. Screening for Compounds which Inhibit IKKα

The present invention provides methods to screen compounds which inhibit phosphorylation of IKKα. These methods are based upon the inventor's discovery that a decrease or absence of phosphorylated IKKα is correlated with a decrease in B cell maturation. Compounds which inhibit phosphorylation can be screened by in vitro assay systems, or by in vivo assay systems. In vitro assay systems include utilizing purified proteins. In vivo assay systems include utilizing cultured cells, cultured tissues or whole multi-cellular organisms. In some embodiments, compounds that inhibit phosphorylation of IKKα are those compounds which decrease phosphorylation of IKKα relative to phosphorylation in the absence of the compound; thus, the absence of the compound is a control. In other embodiments, compounds that inhibit phosphorylation of IKKα are those compounds which decrease phosphorylation of a native IKKα relative to phosphorylation of a control IKKα, where the control IKKα is a modified IKKα which cannot be phosphorylated. Inhibition is a decrease of phosphorylation of typically at least about 10%, and preferably at least about 20%, and more preferably at least about 50%, and even more preferably of at least bout 90%, of control phosphorylation values.

In some embodiments, methods utilizing in vitro screening systems comprise providing a composition comprising IKKα, a phosphorylation source, an IKKα kinase, and a compound to be screened, and detecting phosphorylated IKKα. As described above, NIK is contemplated to be the kinase that phosphorylates IKKα in vivo. Both IKKα and NIK can be prepared by methods well known in the art. For example, IKKα and NIK can be produced in Sf9 cells using baculoviruses; IKKα can be chromatographically purified, and NIK can be immunopurified. It is not necessary that these proteins be highly purified; however, it is desirable that they be free of contaminants that interfere with the assay. In some embodiments, the phosphorylation source comprises a labeled phosphorous group which is transferred to IKKα by NIK; phosphorylation of IKKα is then detected by the presence of the label in association with IKKα. A phosphorylation source can donate a phosphate group to an acceptor by action of a kinase. Exemplary phosphorylation sources include but are not limited to ATP, GTP, and high energy phosphate compounds capable of donating a phosphate group to an acceptor via a kinase. Exemplary sources of a labeled phosphorylation include but are not limited to $[\gamma^{-32}P]ATP$, where the [γ-$^{32}$P] is transferred to IKKα by NIK, and [γ-$^{32}$P]ATP. Phosphorylated IKKα can be detected by well known methods; in one example, when the phosphorylation source comprises a labeled phosphate group, the protein is separated from the soluble phosphorylation source by precipitation, and the amount of radioactivity in the precipitate determined. Phosphorylation of IKKα can be confirmed by separating the proteins by SDS-PAGE, and analyzing the IKKα band for the presence of the phosphate group; in some embodiments, the phosphate group is labeled, and methods of analysis include autoradiography of the separated protein bands.

Screening assays are conducted by contacting (as by mixing) IKKα, NIK, a phosphorylation source, and a compound to be screened. The mixture is incubated for a sufficient period of time, and the proteins are separated from the soluble components, and the amount of radioactivity incorporated determined. Exemplary but non-limiting reaction conditions include, Tris-HCl (pH 7.6) (at about 20 mM), MgCl$_2$ (at about 10 mM), DTT (at about), ATP (at about 0.5 mM, and [γ-$^{32}$P] ATP (at about 5 uCi) at room temperature (see, for example, Ling L et al. (1998) Proc Natl Acad Sci USA 95: 3792-3797). The proteins are added at appropriate quantities; exemplary but non-limiting amounts include about 10 to about 5000 ng. Reaction times can vary, from a few minutes to a few hours; exemplary times include about 30 to about 60 minutes.

Control assays may contain IKKα which can't be phosphorylated; one example is a modified IKKα, in which a substitute amino acid is present at amino acid position 176, at amino acid position 180, or at both amino acid positions. Such an IKKα can be expressed from the IKKα$^{AA}$ allele, as described in Example 4. The components of the assay may be added in any order, although it may be desirable to add the compound to be screened before or after adding the phosphorylation source. It is a matter of routine experimentation to optimize the assay conditions. High through-put screening assays can be designed to screen large numbers of compounds quickly.

In some embodiments, methods utilizing in vivo screening methods comprise providing a first mouse cell comprising native (or wild-type) IKKα, a phosphorylation source and a compound to be screened, contacting the cell with the phosphorylation source and the compound to be screened, and detecting phosphorylated IKKα. In some embodiments, a control is utilized, where the control is a second mouse cell expressing a modified IKKα that is not phosphorylated; exemplary modified IKKαs are described above. In these methods, the second mouse cell expressing the modified IKKα is also contacted with a phosphorylation source and the compound to be screened, and the presence and/or the amounts of phosphorylated modified IKKα is detected and compared to the presence and/or amounts of phosphorylated wild-type IKKα. A mouse cell which expresses a modified IKKα can be prepared as described in Example 4; basically, this mouse cell is prepared by knocking out endogenous (or native or wild-type) IKKα and knocking in the modified IKKα. The phosphorylation source and the means to detect phosphorylated IKKαs are as described above.

In other embodiments, methods utilizing in vivo screening are directed to detecting the amount of NF-κB2 processing (which is also the processing of p100) in the presence or absence of the compound to be screened, or in the presence of the compound to be screened where the IKKα is either native or modified. These methods are based upon the inventor's discovery that a decrease in or absence of phosphorylated IKKα results in decreased processing of NF-κB2, which is contemplated to ultimately prevent B cell maturation. The in vivo screening methods comprise providing a first mouse cell comprising native IKKα and a compound to be screened, contacting the cell with a compound to be screened, and detecting the amount of processed NF-κB2 in the mouse cell. Processed NF-κB2 can be detected by well known methods; and for example, as is described above in the specification and in the Examples and in the description of FIG. 8. The amount of processed NF-κB2 can be compared to the amount observed in a mouse cell in the absence of the compound, thereby detecting inhibition of processing of NF-κB2.

In some embodiments, methods utilizing in vivo screening are directed to detecting the amount of processing of NF-κB2 processing, where the control is a second mouse cell expressing a modified IKKα that is not phosphorylated; exemplary modified IKKαs are described above. In these methods, the second mouse cell expressing the modified IKKα is also contacted with a phosphorylation source and the compound to be screened, and the presence and/or the amounts of phosphorylated modified IKKα is detected and compared to the amounts of phosphorylated native IKKα. A mouse cell which expresses a modified IKKα can be prepared as described in Example 4; basically, this mouse cell is prepared by knocking out endogenous IKKα and knocking in the modified IKKα. The phosphorylation source and the means to detect phosphorylated IKKαs are as described above.

III. Inhibition of IKKα Phosphorylation Prevents B Cell Maturation and Antibody Production The present invention provides means to suppress B cell maturation and antibody production. In particular, the present invention also provides methods for the use of IKK for the specific inhibition of B-cell maturation and antibody production without interfering with innate immunity or T-cell mediated immunity. Thus, the present invention finds use in prevention of diseases associated with antibody-mediated pathology, including but not limited to graft rejection, graft vs. host disease, and autoimmune disease. In addition, the present invention provides means to inhibit the proliferation of B-cell tumors, such as multiple myeloma and chronic lymphocytic leukemia.

The methods of the invention contemplate utilizing an agent which reduces phosphorylation of IKKα in a B cell, thereby reducing maturation of the B cell and/or reducing antibody production by the B cell. The term "phosphorylation of IKKα" refers to the phosphorylation of IKKα observed in IKKα when exposed to the kinase activity of the enzyme NIK.

The terms "reducing phosphorylation of IKKα" when made in reference to the effect of an agent means that the agent reduces the level of phosphorylation of IKKα to a quantity which is preferably 10% less than, more preferably 50% less than, yet more preferably 75% than, even more preferably 90% less than, the quantity of phosphorylation in a corresponding control sample, and most preferably is at the same level which is observed in a control sample. A reduced level of phosphorylation of IKKα need not, although it may, mean an absolute absence of phosphorylation of IKKα. The invention does not require, and is not limited to, methods which wholly eliminate phosphorylation of IKKα. The term "agent" means a molecule that can reduce phosphorylation of IKKα.

1. Antibodies

In one embodiment, the agent which inhibits phosphorylation of IKKα is an antibody. The terms "antibody" and "immunoglobulin" are interchangeably used to refer to a glycoprotein or a portion thereof (including single chain antibodies), which is evoked in an animal by an immunogen and which demonstrates specificity to the immunogen, or, more specifically, to one or more epitopes contained in the immunogen. The term antibody expressly includes within its scope antigen binding fragments of such antibodies, including, for example, Fab, F(ab')2, Fd or Ev fragments of an antibody. The antibodies of the invention also include chimeric and humanized antibodies. Antibodies may be polyclonal or monoclonal. The term "polyclonal antibody" refers to an immunoglobulin produced from more than a single clone of plasma cells; in contrast "monoclonal antibody" refers to an immunoglobulin produced from a single clone of plasma cells.

Antibodies contemplated to be within the scope of the invention include naturally occurring antibodies as well as non-naturally occurring antibodies, including, for example, single chain antibodies, chimeric, bifunctional and humanized antibodies, as well as antigen-binding fragments thereof. Naturally occurring antibodies may be generated in any species including murine, rat, rabbit, hamster, human, and simian species using methods known in the art. Non-naturally occurring antibodies can be constructed using solid phase peptide synthesis, can be produced recombinantly or can be obtained, for example, by screening combinatorial libraries consisting of variable heavy chains and variable light chains as previously described [Huse et al., Science 246:1275Å1281 (1989)]. These and other methods of making, for example, chimeric, humanized, CDRÅgrafted, single chain, and bifunctional antibodies are well known to those skilled in the art (Winter and Harris, Immunol. Today 14:243Å246 (1993); Ward et al., Nature 341:544Å546 (1989); Hilyard et al., Protein Engineering: A practical approach (IRL Press 1992); Borrabeck, Antibody Engineering, 2d ed. (Oxford University Press 1995).

As used herein, the term "antibody" when used in reference to an anti-IKKα antibody refers to an antibody which specifically binds to one or more epitopes on an IKKα polypeptide or peptide portion thereof. In a preferred embodiment, the antibody binds to an epitope on IKKα which contains the amino acids at position 176 and/or position 180 of the IKKα polypeptide. In another embodiment, an anti-IKKα antibody, or antigen binding fragment thereof, is characterized by having specific binding activity for IKKα of at least about $1 \times 10^5$ M−1, more preferably at least about $1 \times 10^6$ M−1, and yet more preferably at least about $1 \times 10^7$ M−1.

Those skilled in the art know how to make polyclonal and monoclonal antibodies which are specific to a desirable polypeptide. For example, monoclonal antibodies may be generated by immunizing an animal (e.g., mouse, rabbit, etc.) with a desired antigen and the spleen cells from the immunized animal are immortalized, commonly by fusion with a myeloma cell.

Immunization with antigen may be accomplished in the presence or absence of an adjuvant, e.g., Freund's adjuvant. Typically, for a mouse, 10_g antigen in 50-200_l adjuvant or aqueous solution is administered per mouse by subcutaneous, intraperitoneal or intra-muscular routes. Booster immunization may be given at intervals, e.g., 2-8 weeks. The final boost is given approximately 2-4 days prior to fusion and is generally given in aqueous form rather than in adjuvant.

Spleen cells from the immunized animals may be prepared by teasing the spleen through a sterile sieve into culture medium at room temperature, or by gently releasing the spleen cells into medium by pressure between the frosted ends of two sterile glass microscope slides. The cells are harvested by centrifugation (400×g for 5 min.), washed and counted.

Spleen cells are fused with myeloma cells to generate hybridoma cell lines. Several mouse myeloma cell lines which have been selected for sensitivity to hypoxanthine-aminopterin-thymidine (HAT) are commercially available and may be grown in, for example, Dulbecco's modified Eagle's medium (DMEM) (Gibco BRL) containing 10-15% fetal calf serum. Fusion of myeloma cells and spleen cells may be accomplished using polyethylene glycol (PEG) or by electrofusion using protocols which are routine in the art. Fused cells are distributed into 96-well plates followed by selection of fused cells by culture for 1-2 weeks in 0.1 ml DMEM containing 10-15% fetal calf serum and HAT. The supernatants are screened for antibody production using methods well known in the art. Hybridoma clones from wells containing cells which produce antibody are obtained, e.g., by limiting dilution. Cloned hybridoma cells (4-5×106) are implanted intraperitoneally in recipient mice, preferably of a BALB/c genetic background. Sera and ascites fluids are collected from mice after 10-14 days.

The invention also contemplates humanized antibodies which are specific for at least a portion of IKKα. Humanized antibodies may be generated using methods known in the art, such as those described in U.S. Pat. Nos. 5,545,806; 5,569, 825 and 5,625,126, the entire contents of which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

2. Nucleic Acid Sequences

In an alternative embodiment, the agent which phosphorylation of IKKα is a nucleic acid sequence. The terms "nucleic acid sequence" and "nucleotide sequence" as used herein refer to two or more nucleotides which are covalently linked to each other. Included within this definition are oligonucleotides, polynucleotide, and fragments or portions thereof, DNA or RNA of genomic or synthetic origin which may be single-stranded or double-stranded, and represent the sense or antisense strand. Nucleic acid sequences which are particularly useful in the instant invention include, without limitation, antisense sequences and ribozymes. The nucleic acid sequences are contemplated to bind to genomic DNA sequences or RNA sequences which encode IKKα thereby reducing phosphorylation of IKKα by NIK. Antisense and ribozyme sequences may be delivered to cells by transfecting the cell with a vector that expresses the antisense nucleic acid or the ribozyme as an mRNA molecule. Alternatively, delivery may be accomplished by entrapping ribozymes and antisense sequences in liposomes.

a. Antisense Sequences

Antisense sequences have been successfully used to inhibit the expression of several genes [Markus-Sekura (1988) Anal. Biochem. 172:289-295; Hambor et al. (1988) J. Exp. Med. 168:1237-1245; and patent EP 140 308], including the gene encoding VCAM1, one of the integrand 4 1 ligands [U.S. Pat. No. 6,252,043, incorporated in its entirety by reference]. The terms "antisense DNA sequence" and "antisense sequence" as used herein interchangeably refer to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Sense mRNA generally is ultimately translated into a polypeptide. Thus an "antisense DNA sequence" is a sequence which has the same sequence as the non-coding strand in a DNA duplex, and which encodes an "antisense RNA," i.e., a ribonucleotide sequence whose sequence is complementary to a "sense mRNA" sequence. The designation (−) (i.e., "negative") is sometimes used in reference to the antisense strand, with the designation (+) sometimes used in reference to the sense (i.e., "positive") strand. Antisense RNA may be produced by any method, including synthesis by splicing an antisense DNA sequence to a promoter which permits the synthesis of antisense RNA. The transcribed antisense RNA strand combines with natural mRNA produced by the cell to form duplexes. These duplexes then block either the further transcription of the mRNA or its translation, or promote its degradation.

Any antisense sequence is contemplated to be within the scope of this invention if it is capable of reducing the level of expression of IKKα to a quantity which is less than the quantity of IKKα expression in a corresponding control tissue which is (a) not treated with the antisense IKKα sequence, (b) treated with a corresponding sense IKKα sequence, or (c) treated with a nonsense sequence.

The terms "reducing the level of expression of IKKα" "diminishing IKKα expression" and grammatical equivalents thereof refer to reducing the level of IKKα expression to a quantity which is preferably 20% less than the quantity in a corresponding control tissue, more preferably is 50% less than the quantity in a corresponding control tissue, yet more preferably is 90% less than the quantity in a corresponding control tissue, and most preferably is at the background level of, or is undetectable by, a Western blot analysis of IKKα, by immunofluorescence for detection of IKKα, by reverse transcription polymerase chain (RT-PCR) reaction for detection of IKKα mRNA, or by in situ hybridization for detection of IKKα mRNA. When a background level or undetectable level of IKKα peptide or mRNA is measured, this may indicate that IKKα is not expressed. A reduced level of IKKα polypeptide or mRNA need not, although it may, mean an absolute absence of expression of IKKα. The invention does not require, and is not limited to, antisense IKKα sequences which eliminate expression of IKKα.

Antisense IKKα sequences capable of reducing the level of IKKα expression include, for example, sequences which are capable of hybridizing with at least a portion of IKKα cDNA under high stringency or low stringency conditions. Low stringency conditions when used in reference to nucleic acid hybridization comprise conditions equivalent to binding or hybridization at 68° C. in a solution consisting of 5×SSPE (43.8 g/l NaCl, 6.9 g/l NaH2PO4_H2O and 1.85 g/l EDTA, pH adjusted to 7.4 with NaOH), 1% SDS, 5× Denhardt's reagent [50× Denhardt's contains the following per 500 ml: 5 g Ficoll (Type 400, Pharmacia), 5 g BSA (Fraction V; Sigma)] and 100_g/ml denatured salmon sperm DNA followed by washing in a solution comprising 0.2×SSPE, and 0.1% SDS at room temperature when a DNA probe of about 100 to about 1000 nucleotides in length is employed. High stringency conditions when used in reference to nucleic acid hybridization comprise conditions equivalent to binding or hybridization at 68° C. in a solution consisting of 5×SSPE, 1% SDS, 5× Denhardt's reagent and 100_g/ml denatured salmon sperm DNA followed by washing in a solution comprising 0.1× SSPE, and 0.1% SDS at 68° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

Antisense IKKα sequences within the scope of this invention may be designed using approaches known in the art. In a preferred embodiment, the antisense IKKα sequences are designed to be hybridizable to IKKα mRNA which is encoded by the coding region of the IKKα gene (Genbank Sequence Accession No. AF080157). Alternatively, antisense IKKα sequences may be designed to reduce transcription by hybridizing to upstream nontranslated sequences, thereby preventing promoter binding to transcription factors.

In a preferred embodiment, the antisense sequences of the invention range in size from about 8 to about 100 nucleotide residues. In yet a more preferred embodiment, the antisense sequences range in size from about 8 to about 30 nucleotide residues. In a most preferred embodiment, the antisense sequences have 20 nucleotide residues.

However, the invention is not intended to be limited to the number of nucleotide residues in the antisense sequence. Any oligonucleotide sequence which is capable of reducing expression of IKKα is contemplated to be within the scope of this invention. For example, oligonucleotide sequences may range in size from about 3 nucleotide residues to the entire IKKα cDNA sequence. The art skilled know that the degree of sequence uniqueness decreases with decreasing length, thereby reducing the specificity of the oligonucleotide for the IKKα mRNA.

The antisense oligonucleotide sequences which are useful in the methods of the instant invention may comprise naturally occurring nucleotide residues as well as nucleotide analogs. Nucleotide analogs may include, for example, nucleotide residues which contain altered sugar moieties, altered inter-sugar linkages (e.g., substitution of the phosphodiester bonds of the oligonucleotide with sulfur-containing bonds, phosphorothioate bonds, alkyl phosphorothioate bonds, N-alkyl phosphoramidates, phosphorodithioates, alkyl phosphonates and short chain alkyl or cycloalkyl structures), or altered base units. Oligonucleotide analogs are desirable, for example, to increase the stability of the antisense oligonucleotide compositions under biologic conditions since natural phosphodiester bonds are not resistant to nuclease hydrolysis. Oligonucleotide analogs may also be desirable to improve incorporation efficiency of the oligonucleotides into liposomes, to enhance the ability of the compositions to penetrate into the cells where the nucleic acid sequence whose activity is to be modulated is located, in order to reduce the amount of antisense oligonucleotide needed for a therapeutic effect thereby also reducing the cost and possible side effects of treatment.

Antisense oligonucleotide sequences may be synthesized using any of a number of methods known in the art, as well as using commercially available services (e.g., Genta, Inc.). Synthesis of antisense oligonucleotides may be performed, for example, using a solid support and commercially available DNA synthesizers. Alternatively, antisense oligonucleotides may also be synthesized using standard phosphoramidate chemistry techniques. For example, it is known in the art that for the generation of phosphodiester linkages, the oxidation is mediated via iodine, while for the synthesis of phosphorothioates, the oxidation is mediated with 3H-1,2-benzodithiole-3-one,1,-dioxide in acetonitrile for the step-wise thioation of the phosphite linkages. The thioation step is followed by a capping step, cleavage from the solid support, and purification on HPLC, e.g., on a PRP-1 column and gradient of acetonitrile in triethylammonium acetate, pH 7.0.

In one embodiment, the antisense DNA sequence is an "IKKα antisense DNA sequence," i.e., an antisense DNA sequence which is designed to bind with at least a portion of the IKKα genomic sequence or with IKKα mRNA. The design of IKKα antisense DNA sequences is facilitated by the availability of the sequences for the IKKα cDNA (FIG. 9; Genbank sequence Accession No. AF080157). Particularly preferred antisense sequences are those which hybridize with genomic DNA or with RNA encoding a portion of IKKα which is phosphorylated by NIK. Such integrin 4 1 portions are exemplified by, but not limited to, sequences which target nucleotide sequences that encode the amino acids at position 176 and/or position 180 of the IKKα protein.

b. Ribozyme

In an alternative embodiment, the agent which reduces phosphorylation of IKKα (e.g., by NIK) is a ribozyme. Ribozyme sequences have been successfully used to inhibit the expression of several genes, such as the gene encoding VCAM1 [U.S. Pat. No. 6,252,043, incorporated in its entirety by reference].

The term "ribozyme" refers to an RNA sequence that hybridizes to a complementary sequence in a substrate RNA and cleaves the substrate RNA in a sequence specific manner at a substrate cleavage site. Typically, a ribozyme contains a "catalytic region" flanked by two "binding regions." The ribozyme binding regions hybridize to the substrate RNA, while the catalytic region cleaves the substrate RNA at a "substrate cleavage site" to yield a "cleaved RNA product." The nucleotide sequence of the ribozyme binding regions may be completely complementary or partially complementary to the substrate RNA sequence with which the ribozyme binding regions hybridize. Complete complementarity is preferred in order to increase the specificity, as well as the turnover rate (i.e., the rate of release of the ribozyme from the cleaved RNA product), of the ribozyme. Partial complementarity, while less preferred, may be used to design a ribozyme binding region containing more than about 10 nucleotides. While contemplated to be within the scope of the claimed invention, partial complementarity is generally less preferred than complete complementarity since a binding region having partial complementarity to a substrate RNA exhibits reduced specificity and turnover rate of the ribozyme when compared to the specificity and turnover rate of a ribozyme which contains a binding region having complete complementarity to the substrate RNA. A ribozyme may hybridize to a partially or completely complementary DNA sequence but cannot cleave the hybridized DNA sequence since ribozyme cleavage requires a 2'-OH on the target molecule, which is not available on DNA sequences.

The ability of a ribozyme to cleave at a substrate cleavage site may readily be determined using methods known in the art. These methods include, but are not limited to, the detection (e.g., by Northern blot analysis as described herein, reverse-transcription polymerase chain reaction (RT-PCR), in situ hybridization and the like) of reduced in vitro or in vivo levels of RNA which contains a ribozyme substrate cleavage site for which the ribozyme is specific, compared to the level of RNA in controls (e.g., in the absence of ribozyme, or in the presence of a ribozyme sequence which contains a mutation in one or both unpaired nucleotide sequences which renders the ribozyme incapable of cleaving a substrate RNA).

Ribozymes contemplated to be within the scope of this invention include, but are not restricted to, hammerhead ribozymes [see, e.g., Reddy et al., U.S. Pat. No. 5,246,921; Taira et al., U.S. Pat. No. 5,500,357, Goldberg et al., U.S. Pat. No. 5,225,347, the contents of each of which are herein incorporated by reference], Group I intron ribozyme [Kruger et al. (1982) Cell 31: 147-157], ribonuclease P [Guerrier-Takada et al. (1983) Cell 35: 849-857], hairpin ribozyme [Hampel et al., U.S. Pat. No. 5,527,895 incorporated by reference], and hepatitis delta virus ribozyme [Wu et al. (1989) Science 243:652-655].

A ribozyme may be designed to cleave at a substrate cleavage site in any substrate RNA so long as the substrate RNA contains one or more substrate cleavage sequences, and the sequences flanking the substrate cleavage site are known. Expression in vivo of such ribozymes and the resulting cleavage of RNA transcripts of a gene of interest would in effect reduce or ablate expression of the corresponding gene.

For example, where the ribozyme is a hammerhead ribozyme, the basic principle of a hammerhead ribozyme design involves selection of a region in the substrate RNA which contains a substrate cleavage sequence, creation of two stretches of antisense oligonucleotides (i.e., the binding regions) which hybridize to sequences flanking the substrate cleavage sequence, and placing a sequence which forms a hammerhead catalytic region between the two binding regions.

In order to select a region in the substrate RNA which contains candidate substrate cleavage sites, the sequence of the substrate RNA needs to be determined. The sequence of RNA encoded by a genomic sequence of interest is readily determined using methods known in the art. For example, the sequence of an RNA transcript may be arrived at either manually, or using available computer programs (e.g., GENEWORKS, from IntelliGenetic Inc., or RNADRAW available from the internet at ole@mango.mef.ki.se), by changing the T in the DNA sequence encoding the RNA transcript to a U.

Substrate cleavage sequences in the target RNA may by located by searching the RNA sequence using available computer programs. For example, where the ribozyme is a hammerhead ribozyme, it is known in the art that the catalytic region of the hammerhead ribozyme cleaves only at a substrate cleavage site which contains a NUH, where N is any nucleotide, U is a uridine, and H is a cytosine (C), uridine (U), or adenine (A) but not a guanine (G). The U-H doublet in the NUH cleavage site does not include a U-G doublet since a G would pair with the adjacent C in the ribozyme and prevent ribozyme cleavage. Typically, N is a G and H is a C. Consequently, GUC has been found to be the most efficient substrate cleavage site for hammerhead ribozymes, although ribozyme cleavage at CUC is also efficient.

In a preferred embodiment, the substrate cleavage sequence is located in a loop structure or in an unpaired region of the substrate RNA. Computer programs for the prediction of RNA secondary structure formation are known in the art and include, for example, "RNADRAW" [ole@mango.mef.ki.se], "RNAFOLD" [Hofacker et al. (1994) Monatshefte F. Chemie 125:167-188; McCaskill (1990) Biopolymers 29:1105-1119]. "DNASIS" (Hitachi), and The Vienna Package [ftp://nrcbsa.bio.nrc.ca/pub and ftp://ftp.itc.univie.ac.at].

In addition to the desirability of selecting substrate cleavage sequences which are located in a loop structure or an unpaired region of the substrate RNA, it is also desirable, though not required, that the substrate cleavage sequence be located downstream (i.e., at the 3'-end) of the translation start codon (AUG or GUG) such that the translated truncated polypeptide is not biologically functional.

In a preferred embodiment, the ribozyme is an "IKKα ribozyme", i.e., a ribozyme whose substrate cleavage sequence is designed to hybridize with an mRNA which codes for a portion of IKKα that is phosphorylated by NIK. Such IKKα portions are exemplified by, but not limited to, sequences which contain the amino acid at position 176 and/or position 180 of the IKKα protein.

It is known in the art that the specificity of ribozyme cleavage for a substrate RNA molecule is determined by the sequence of nucleotides which flank the substrate cleavage site and which hybridize with the ribozyme binding regions. Thus, ribozymes can be designed to cleave at different locations within a substrate RNA molecule by altering the sequence of the binding regions that surround the ribozyme catalytic region of the ribozyme such that the binding regions hybridize with any known sequence on the substrate RNA.

In addition to varying the sequence of the binding regions to effect binding to different locations on the RNA substrate, the number of nucleotides in each of the ribozyme binding regions may also be altered in order to change the specificity of the ribozyme for a given location on the RNA substrate. The number of nucleotides in a binding region is preferably between about 5 and about 25 nucleotides, more preferably between about 11 and about 15 nucleotides, yet more preferably between about 7 nucleotides and about 10 nucleotides.

One of skill in the art appreciates that it is not necessary that the two binding regions which flank the ribozyme catalytic region be of equal length. Binding regions which contain any number of nucleotides are contemplated to be within the scope of this invention so long as the desirable specificity of the ribozyme for the RNA substrate and the desirable cleavage rate of the RNA substrate are achieved. One of skill in the art knows that binding regions of longer nucleotide sequence, while increasing the specificity for a particular substrate RNA sequence, may reduce the ability of the ribozyme to dissociate from the substrate RNA following cleavage to bind with another substrate RNA molecule, thus reducing the rate of cleavage. On the other hand, though binding regions with shorter nucleotide sequences may have a higher rate of dissociation and cleavage, specificity for a substrate cleavage site may be compromised.

It is well within the skill of the art to determine an optimal length for the binding regions of a ribozyme such that a desirable specificity and rate of cleavage are achieved. Both the specificity of a ribozyme for a substrate RNA and the rate of cleavage of a substrate RNA by a ribozyme may be determined by, for example, kinetic studies in combination with Northern blot analysis or nuclease protection assays.

In a preferred embodiment, the complementarity between the ribozyme binding regions and the substrate RNA is complete. However, the invention is not limited to ribozyme sequences in which the binding regions show complete complementarity with the substrate RNA. Complementarity may be partial so long as the desired specificity of the ribozyme for a substrate cleavage site, and the rate of cleavage of the substrate RNA are achieved. Thus, base changes may be made in one or both of the ribozyme binding regions as long as substantial base pairing with the substrate RNA in the regions flanking the substrate cleavage sequence is maintained and base pairing with the substrate cleavage sequence is minimized. The term "substantial base pairing" means that greater than about 65%, more preferably greater than about 75%, and yet more preferably greater than about 90% of the bases of the hybridized sequences are base-paired.

It may be desirable to increase the intracellular stability of ribozymes expressed by an expression vector. This is achieved by designing the expressed ribozyme such that it contains a secondary structure (e.g., stem-loop structures) within the ribozyme molecule. Secondary structures which are suitable for stabilizing ribozymes include, but are not limited to, stem-loop structures formed by intraÄstrand base pairs. An alternative to the use of a stem-loop structure to protect ribozymes against ribonuclease degradation is by the insertion of a stem loop at each end of the ribozyme sequence [Sioud and Drlica (1991) Proc. Natl. Acad. Sci. USA 88:7303-7307]. Other secondary structures which are useful in reducing the susceptibility of a ribozyme to ribonuclease degradation include hairpin, bulge loop, interior loop, multi-branched loop, and pseudoknot structure as described in "Molecular and Cellular Biology," Stephen L. Wolfe (Ed.), Wadsworth Publishing Company (1993) p. 575. Additionally, circularization of the ribozyme molecule protects against ribonuclease degradation since exonuclease degradation is initiated at either the 5-end or 3-end of the RNA. Methods of expressing a circularized RNA are known in the art [see, e.g., Puttaraju et al. (1993) Nucl. Acids Res. 21:4253-4258].

Once a ribozyme with desirable binding regions, a catalytic region and nuclease stability has been designed, the ribozyme may be produced by any known means including chemical synthesis. Chemically synthesized ribozymes may be introduced into a cell by, for example, microinjection, electroporation, lipofection, etc. In a preferred embodiment, ribozymes are produced by expression from an expression vector which contains a gene encoding the designed ribozyme sequence.

3. Other Agents

In addition to antibody and nucleic acid sequences which reduce phosphorylation of IKKα, the invention also expressly contemplates within its scope other agents (e.g., organic molecules, inorganic molecules, etc.) so long as the agent is capable of reducing phosphorylation of IKKα. Such agents may be identified by screening libraries of test compounds as described herein.

4. Reducing the Severity of a Pathological Condition Associated with Antibody Production and/or B Cell Maturation The invention provides methods for inhibiting undesirable pathological conditions associates with antibody and/or B cell maturation in a subject by reducing phosphorylation of IKKα in B cells in the subject.

The term "pathological condition" is used broadly herein to mean any abnormal physical or physiological condition which is associated, at least in part, by undesirable antibody production as exemplified by, but not limited to, transplantation rejection and autoimmune diseases. Alternatively, the pathological condition may be associated with undesirable B cell maturation, such as that observed in B cell tumors which are exemplified by, but not limited to, leukemia. The terms "neoplasm" and "tumor" refer to undesirable tissue growth which may be benign or malignant. The terms "malignant neoplasm" and "malignant tumor" refer to a neoplasm which contains at least one cancer cell. A "cancer cell" refers to a cell undergoing early, intermediate or advanced stages of multi-step neoplastic progression as previously described [H. C. Pitot (1978) in "Fundamentals of Oncology," Marcel Dekker (Ed.), New York pp 15-28]. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. A cell in the early stages of malignant progression is referred to as "hyperplastic cell" and is characterized by dividing without control and/or at a greater rate than a normal cell of the same cell type in the same tissue. Proliferation may be slow or rapid but continues unabated. A cell in the intermediate stages of neoplastic progression is referred to as a "dysplastic cell." A dysplastic cell resembles an immature epithelial cell, is generally spatially disorganized within the tissue and loses its specialized structures and functions. During the intermediate stages of neoplastic progression, an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive i.e., they either invade adjacent tissues, or are shed from the primary site and circulate through the blood and lymph to other locations in the body where they initiate one or more secondary cancers, i.e., "metastases." Thus, the term "cancer" is used herein to refer to a malignant neoplasm, which may or may not be metastatic.

The terms "reducing the severity of a pathological condition," "diminishing the severity of a pathological condition, "reducing symptoms associated with a pathological condition" mean that adverse clinical signs or symptoms associated with the pathological condition are reduced, delayed, or eliminated as compared to the level of the pathological condition in the absence of treatment with the particular composition or method. The effects of diminishing the severity of a pathological condition may be determined by methods routine to those skilled in the art including, but not limited to, angiography, ultrasonic evaluation, fluoroscopic imaging, fiber optic endoscopic examination, biopsy and histology, blood tests, which can be used to determine relevant enzyme levels or circulating antigen or antibody, imaging tests which can be used to detect a decrease in the growth rate or size of a neoplasm, or an ophthalmic procedure which can be used to identify a reduction in the number of blood vessels in the retina of a diabetic patient. Such clinical tests are selected based on the particular pathological condition being treated. A reduction in the severity of a pathological condition also can be detected based on subjective comments made by the patient being treated One skilled in the art would know that agents within the scope of this invention can be administered by various routes including, for example, orally, intranasally, or parenterally, including intravenously, intramuscularly, subcutaneously, intraorbitally, intracapsularly, intrasynovially, intraperitoneally, intracisternally or by passive or facilitated absorption through the skin using, for example, a skin patch or transdermal iontophoresis. Furthermore, the agent can be administered by injection, intubation, via a suppository, orally or topically, the latter of which can be passive, for example, by direct application of an ointment or powder containing the agent, or active, for example, using a nasal spray or inhalant. The agent can also be administered as a topical spray, if desired, in which case one component of the composition is an appropriate propellant. The pharmaceutical composition also can be incorporated, if desired, into liposomes, microspheres or other polymer matrices [Gregoriadis, "Liposome Technology," Vol. 1, CRC Press, Boca Raton, Fla. 1984]. Liposomes, for example, which consist of phospholipids or other lipids, are nontoxic, physiologically acceptable and metabolizable carriers that are relatively simple to make and administer. Liposomes are lipid-containing vesicles having a lipid bilayer as well as other lipid carrier particles which can entrap chemical agents. Liposomes may be made of one or more phospholipids, optionally including other materials such as sterols. Suitable phospholipids include phosphatidyl cholines, phosphatidyl serines, and many others that are well known in the art. Liposomes can be unilamellar, multilamellar or have an undefined lamellar structure.

Agents which reduce phosphorylation of IKKα may be administered in conjunction with other therapies. For example, in the case of leukemia therapy, the agent may be administered in conjunction with conventional drug therapy and/or chemotherapy which is directed against leukemia and for control of establishment of metastases. In one embodiment, the agent is administered during or after chemotherapy. In an alternative embodiment, the agent may be administered after surgery in which solid tumors have been removed as a prophylaxis against future metastases.

An agent is administered in a "therapeutic amount," i.e., in an amount which is sufficient to achieve a desired result. In particular, a therapeutic amount is that amount which inhibits the phosphorylation of IKKα in B cells and which results in the reduction, delay, or elimination of undesirable pathologic effects in the subject. One of ordinary skill recognizes that a "therapeutically effective" amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

A therapeutic amount may be determined using in vitro and in vivo assays known in the art and disclosed herein. These are exemplified, without limitation, to administering different amounts of the agent to determine reduction of phosphorylation of IKKα. Generally, an agent is administered in a dose of about 0.0001 to 100 mg/kg body weight.

The "subject" to whom the agents are administered includes any mammal which produces B cells, including, without limitation, human and non-human animals such simian, rodent, ovine, bovine, ruminant, lagomorph, porcine, caprine, equine, canine, feline, ave, and the like. Preferred non-human animals are selected from the order Rodentia (e.g., mouse and rat). Thus the compounds of the invention may be administered by human health professionals as well as veterinarians.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: C (degrees Centigrade); rpm (revolutions per minute); BSA (bovine serum albumin); CFA (complete Freund's adjuvant); IFA (incomplete Freund's adjuvant); IgG (immunoglobulin G); IM (intramuscular); IP (intraperitoneal); IV (intravenous or intravascular); SC (subcutaneous); $H_2O$ (water); HCl (hydrochloric acid); aa (amino acid); bp (base pair); kb (kilobase pair); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); μM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); PMSF (phenylmethylsulfonyl fluoride); RT-PCR (reverse transcription PCR); SDS (sodium dodecyl sulfate); Tris (tris(hydroxymethyl)aminomethane); w/v (weight to volume); v/v (volume to volume); Amersham (Amersham Life Science, Inc. Arlington Heights, Ill.); ICN (ICN Pharmaceuticals, Inc., Costa Mesa, Calif.); Amicon (Amicon, Inc., Beverly, Mass.); ATCC (American Type Culture Collection, Rockville, Md.); Becton Dickinson (Becton Dickinson Labware, Lincoln Park, N.J.); BioRad (BioRad, Richmond, Calif.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Invitrogen (Invitrogen Corp., San Diego, Calif.); New England Biolabs (New England Biolabs, Inc., Beverly, Mass.); Novagen (Novagen, Inc., Madison, Wis.); Pharmacia (Pharmacia, Inc., Piscataway, N.J.); Sigma (Sigma Chemical Co., St. Louis, Mo.); Stratagene (Stratagene Cloning Systems, La Jolla, Calif.); Nuclear factor kappa B (NF-κB); Inhibitor of κB (IκB); IκB kinase (IKK); two catalytic subunits of IKK: IKKα and IKKβ; a regulatory subunit of IKK:IKKγ, also called NEMO; MAP kinase kinase kinase (MAPKKK); NF-γB inducing kinase (NIK, an MAPKKK).

EXAMPLE 1

Analysis of Cell Turnover

In these experiments, cell turnover was analyzed by administering 100 μg/1 g body weight BrdU (Sigma) in the drinking water of test mice for 7 days. On day 8, cells were harvested from the spleen of test and control animals. DNA-incorporated BrdU was detected using flow cytometry, after staining the cells with the FITC-labeled antibody BU-1 (Becton-Dickinson). For this purpose, cells were fixed for 20 minutes with 0.5% paraformaldehyde (PFA) and then permeabilized with 3 N HCl containing 0.5% Tween-20, followed by neutralization with 0.1 M disodiumtetraborate. Cells were stained with FITC-BU-1 in the presence of 0.5% Tween-20. BrdU incorporation into B-cells was identified by pre-staining with anti-IgM (PE, R6-60.2, Pharmingen) and anti-IgD (11-26c.2a, Pharmingen) and anti-rat IgG (F(ab')$_2$, TC, Caltag). Bone marrow cells from untreated and BrdU-treated mice served as negative and positive controls respectively, for flow cytometric analysis. The results of these experiments are indicated in FIG. 2.

As indicated, Ikkα$^{-/-}$ B-cells incorporated between one-third (bone marrow) and two-fold (spleen) more BrdU than wt B cells, as shown in FIG. 2, Panel A. This difference tended to be more pronounced in mature (i.e., IgM$^{lo}$IgD$^{hi}$), rather than virgin (IgM$^{hi}$) B-cells (See, FIG. 2, Panel A). Given the fact that only few IgD$^+$ cells were detectable in Ikkα$^{-/-}$ reconstituted lymph nodes, the smaller difference in the number of BrdU$^+$IgD$^+$ wt and Ikkα$^{-/-}$ cells was somewhat surprising (See, FIG. 2, Panel B). Although an understanding of the mechanism(s) is not necessary in order to use the present invention and it is not intended that the present invention be limited to any particular mechanism, it is contemplated that this result may be caused by high B cell turnover in the spleen, leading to a lower fraction of circulating mature B-cells (See, FIG. 2, Panel B). Consequently, the frequency of mature IgD$^+$ B-cells was found to be significantly lower in Ikkα$^{-/-}$ lymph nodes, as indicated in FIG. 2, Panel C

EXAMPLE 2

Analysis of Lymphoid Organs

In these experiments, lymphoid organs were harvested from test and control animals, and then fixed in 10% buffered formalin and embedded in paraffin. After routine processing, sections were stained with hematoxylin and eosin (H&E) for histological analysis. TUNEL (terminal deoxynucleotidyl transferase-mediated dUTP nick-end labeling) staining was performed using the "In Situ Cell Detection" kit (Boehringer Mannheim).

To analyze GC formation, mice were intraperitoneally injected with 100 mg DNP-KLH absorbed to alum (Calbiochem) and spleens were collected 14 days later. Cryosections were stained with biotinylated peanut agglutinin (Vector), incubated with streptavidin peroxidase (Jackson) for 30 minutes and developed using the Leinco Technologies 3,3'-diaminobenzidine (DAB) kit. Sections were counterstained with hematoxylin (Sigma). To visualize Peyer's patches, the intestines were fixed in PFA, rinsed and dehydrated in a methanol series, as known in the art. Hydrogen peroxide was used to inactivate endogenous peroxidase. After rehydration and blocking, the tissue was stained with anti-VCAM1 antibody (Pharmingen), followed by staining with a secondary goat anti-rat IgG conjugated to horseradish peroxidase. After washing, the tissue was developed with the DAB kit indicated above.

EXAMPLE 3

Differential Requirement for IKKα and IKKβ in Lymphoid Development

In this Example, experiments conducted to analyze bone marrow cells from wild-type, Ikkα$^{-/-}$, and Ikkβ$^{AA}$ embryos are described. Fetal livers were harvested from E16 wt, Ikkα$^{-/-}$, and Ikkβ$^{AA}$ embryos as known in the art (See, Senftleben et al., supra). Genomic DNA was genotyped by PCR with IKKα-specific primers, using methods known in the art (See e.g., Hu et al. Science 284:316 [1999]).

Single cell suspensions were prepared and injected into the tail veins of lethally irradiated 8-week old C57BL/6-CD45 female mice (See, Senftleben et al., supra). The mice were maintained for at least 6 weeks and then sacrificed. The donor origin of the analyzed cells was verified using CD45.2 staining (See, Senftleben et al., supra). The results of these analyses revealed the complete absence of B-cells in the Ikkβ$^{-/-}$ derived samples, as shown in FIG. 1, Panel A. This was confirmed by the absence of immunoglobulin heavy chain gene rearrangement in the bone marrow cells of these animals.

In contrast, B cells were present in Ikkα$^{-/-}$ bone marrow (See, FIG. 1, Panel A). Although these cells expressed normal levels of early B cell markers, a B220$^{hi}$CD24$^{lo}$ population, representing circulating mature B cells, was absent. Ikkβ$^{-/-}$ spleen and lymph nodes lacked lymphoid cells and exhibited very abnormal architecture, while Ikkα$^{-/-}$ reconstituted spleen and lymph nodes appeared to be grossly normal. However, flow cytometric analysis revealed low frequency of B220$^+$ cells in the latter, as shown in FIG. 1, Panel B. No differences in thymocytes and peripheral T-cell populations were found between wt and Ikkα$^{-/-}$ radiation chimeras. This is in marked contrast to the Ikkβ$^{-/-}$ radiation chimeras, which completely lack B and T cells (Senftleben et al., supra). Analysis of typical B cell markers in Ikkα$^{-/-}$ spleen and lymph nodes revealed a pronounced reduction of the mature IgM$^{lo}$IgD$^{hi}$ population compared to virgin IgM$^{hi}$ B cells (See, FIG. 1, Panel B). Whereas the splenic B to T-cell ratio was almost normal six weeks after reconstitution with Ikkα$^{-/-}$ stem cells, it was significantly reduced thereafter (See, FIG. 1, Panel C). The loss of mature IgM$^{lo}$IgD$^{hi}$ cells makes the largest contribution to the paucity of B cells in Ikkα$^{-/-}$ radiation chimeras (FIG. 1, Panel D). This defect in B lymphopoie-

EXAMPLE 4

Construction of the Ikkα$^{AA}$ Mice

In this Example, construction of the Ikkα$^{AA}$ allele is described. A targeting vector in which the codons for serines 176 and 180 in the activation loop of Ikkα were replaced by alanine codons was used to construct the Ikkα$^{AA}$ allele. As indicated below, Ikkα$^{AA}$ mice are viable, fertile, and morphologically indistinguishable from wt mice.

A phage clone containing the genomic sequence of mouse IKKα was used to make the construct. This clone contained the exon that encodes the activation loop with the two serines (S176 and S180) that were mutagenized. A 6.0 kb BamHI fragment from this clone that contained 1.3 kb of DNA upstream to codon 176 and 4.7 kb downstream to it was subclone into pUC18. Within the intron between codons 230 and 231, a NotI site was introduced by site-directed mutagenesis, followed by insertion of a NotI fragment containing the Neo cassette flanked by two loxP sites. Separately, the 6.0 kb BamHI fragment within pUC18 was mutagenized at codons 176 and 180 to alanines, using the Quick Change Site-directed Mutagenesis kit (Stratagene). To minimize the random mutation caused by PCR, a 200 bp BclI-NcoI fragment covering the mutagenized region was sequenced to exclude any other mutations, and then swapped back into the pUC18 clone that contained Neo in the intron. When designing the mutagenic primers, a new Eco47III site was introduced as a marker for S176A/S180A mutation.

The constructs were linearized by digestion at a HindIII site, located after the right arm, and electroporated into ES cells. Approximately 150 G418 resistant ES clones were collected and subjected to PCR analysis to identify those that had integrated the construct at the IKKα locus. Subsequent digestion of the PCR product with Eco47III gave two bands. Six positive clones for the mutations were identified. To eliminate the effects of the Neo gene on the splicing of the IKKα transcript, positive ES clones were grown up and electroporated with a plasmid containing Cre recombinase to delete the Neo gene from the IKKα locus. Positive clones were identified by PCR analysis that was negative for Neo.

An ES clone that was positive for the mutation was injected into blastocysts taken from a donor female mouse at the UCSD core facility for knockout mice. The injected blastocysts were transplanted into a pseudopregnant foster mother, who gave birth to chimeric offspring. Two male chimeric mice with high levels of mosaicism exhibited germline transmission on the first cross with wild-type BL/6 females, generating heterozygotes. Heterozygous males and females were intercrossed, in order to obtain homozygous mutant mice. The genotypes were determined by PCR analysis using tail lysates. The frequency of homozygotes was approximately 25%, as expected.

Mutant mice were normal from birth until adulthood in terms of weight, size, appearance, development, fertility and behavior. These animals were indistinguishable from their heterozygous or wild-type littermates. In contrast to the IKKα knockout mice, these mice showed no defects in skin or limb development. These results indicate that IKKα has at least dual functions in murine development. Indeed, based on these results, IKKα's functions as a protein kinase appear to be independent of its functions associated with other protein domains. However, an understanding of the mechanism(s) involved is not necessary in order to use the present invention.

From the above, it is clear that the present invention provides means to suppress B cell maturation and antibody production. In particular, the present invention also provides methods for the use of IKK for the specific inhibition of B-cell maturation and antibody production without interfering with innate immunity or T-cell mediated immunity. Thus, the present invention finds use in prevention of diseases associated with antibody-mediated pathology, including but not limited to graft rejection, graft vs. host disease, and autoimmune disease. In addition, the present invention provides means to inhibit the proliferation of B-cell tumors, such as multiple myeloma and chronic lymphocytic leukemia.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and/or related fields are intended to be within the scope of the present invention.

The invention claimed is:

1. A method of screening a compound for reducing development of humoral immunity, comprising
a) providing:
i) B lymphocytes comprising IκB kinaseα (IKKα) comprising a sequence set forth in SEQ ID NO:1; and
ii) a compound to be screened;
b) contacting said B lymphocytes with said compound;
c) detecting a reduced level of IKKα protein kinase activity in said B lymphocytes in the presence of said compound, thereby identifying said test compound as reducing development of humoral immunity.

2. The method of claim 1, wherein said reducing development of humoral immunity comprises reducing B lymphocyte maturation.

3. The method of claim 1, wherein said method further comprises identifying said test compound as not reducing the ratio of B lymphocytes to T lymphocytes.

4. The method of claim 1, wherein said detecting of IKKα protein kinase activity comprises detecting IκBα kinase activity.

5. The method of claim 1, wherein said detecting of IKKα protein kinase activity comprises detecting phosphorylation of serine at amino acid position 176 of said SEQ ID NO:1.

6. The method of claim 1, wherein said detecting of IKKα protein kinase activity comprises detecting phosphorylation of seine at amino acid position 180 of said SEQ ID NO:1.

7. The method of claim 1, wherein said detecting of IKKα protein kinase activity comprises detecting phosphorylation of seine at amino acid positions 176 and 180 of said SEQ ID NO:1.

8. The method of claim 1, wherein said B lymphocytes comprise spleen B lymphocytes.

9. The method of claim 1, wherein said B lymphocytes comprise lymph node B lymphocytes.

10. The method of claim 1, wherein said B lymphocytes comprise bone marrow B lymphocytes.

11. The method of claim 1, wherein said IKKα is encoded by a nucleotide sequence set forth as SEQ ID NO:2.

12. The method of claim 1, wherein said IKKα is encoded by a nucleotide sequence which hybridizes to the complement of the sequence set forth in SEQ ID NO:2 under high stringency conditions equivalent to hybridization at 68° C. in a solution
consisting of 5×SSPE, 1% SDS, 5× Denhardt's reagent and 100 µg/ml denatured salmon sperm DNA followed by washing in a solution comprising in 0.1×SSPE and 0.1% SDS at 68° C., and wherein said IKKα comprises IKKα kinase activity.

* * * * *